US008336839B2

(12) United States Patent
Boccoleri et al.

(10) Patent No.: US 8,336,839 B2
(45) Date of Patent: Dec. 25, 2012

(54) MEDICAL EQUIPMENT TRANSFER ARRANGEMENT

(75) Inventors: Gianni R. Boccoleri, Lantana, TX (US); Wojciech Timoszyk, Flower Mound, TX (US); Shibu Korula, Lewisville, TX (US)

(73) Assignee: Stryker Corporation, Kalamazoo, MI (US)

( * ) Notice: Subject to any disclaimer, the term of this patent is extended or adjusted under 35 U.S.C. 154(b) by 494 days.

(21) Appl. No.: 12/310,712

(22) PCT Filed: Oct. 1, 2007

(86) PCT No.: PCT/US2007/021109
§ 371 (c)(1),
(2), (4) Date: Mar. 4, 2009

(87) PCT Pub. No.: WO2008/042346
PCT Pub. Date: Apr. 10, 2008

(65) Prior Publication Data
US 2009/0314923 A1    Dec. 24, 2009

Related U.S. Application Data

(60) Provisional application No. 60/847,838, filed on Sep. 28, 2006, provisional application No. 60/937,398, filed on Jun. 27, 2007.

(51) Int. Cl.
*E04G 3/00*            (2006.01)
(52) U.S. Cl. ........... 248/276.1; 248/280.11; 248/297.11; 248/292.11
(58) Field of Classification Search ............... 248/122.1, 248/123.11, 162.1, 176.1, 176.3, 274.1, 276.1, 248/280.11, 297.11, 292.11, 682, 647, 648, 248/220.21, 220.22, 218.4, 229.15, 229.25, 248/227.3, 228.6, 230.6, 231.71, 309.1; 600/429; 606/130
See application file for complete search history.

(56) References Cited

U.S. PATENT DOCUMENTS

| | | | |
|---|---|---|---|
| 3,390,897 | A | 7/1968 | Moore |
| 4,325,061 | A | 4/1982 | Wolar |
| 4,403,214 | A | 9/1983 | Wolar |
| 4,629,074 | A | 12/1986 | Toder |
| 4,725,027 | A | 2/1988 | Bekanich |

(Continued)

FOREIGN PATENT DOCUMENTS
EP          1 647 251 A1      4/2006
(Continued)

OTHER PUBLICATIONS

International Search Report and Written Opinion dated Mar. 26, 2008.

(Continued)

*Primary Examiner* — Ramon Ramirez
*Assistant Examiner* — Todd M Epps
(74) *Attorney, Agent, or Firm* — Flynn, Thiel, Boutell & Tanis, P.C.

(57) ABSTRACT

An arrangement for transferring a post assembly carrying medical equipment thereon between first and second support structures. The arrangement includes a positioning arm which is supported at one end on the first support structure and at the opposite end is configured for supporting the post assembly. The positioning arm cooperates with a receiver assembly provided on the second support structure. A freestanding cart and wheelchair are also provided which are configured to accept the post assembly from a support structure such as a patient bed, to allow the patient to ambulate with the associated medical equipment.

21 Claims, 25 Drawing Sheets

U.S. PATENT DOCUMENTS

| | | | |
|---|---|---|---|
| D298,460 S | 11/1988 | Pryor | |
| 4,905,944 A | 3/1990 | Jost et al. | |
| 4,945,592 A | 8/1990 | Sims et al. | |
| 4,969,768 A | 11/1990 | Young | |
| 5,072,906 A | 12/1991 | Foster | |
| 5,108,064 A | 4/1992 | Kreuzer | |
| 5,110,076 A | 5/1992 | Snyder et al. | |
| 5,118,127 A | 6/1992 | Partington | |
| 5,135,191 A | 8/1992 | Schmuhl | |
| 5,186,337 A | 2/1993 | Foster et al. | |
| 5,284,255 A | 2/1994 | Foster et al. | |
| 5,299,338 A | 4/1994 | Foster | |
| 5,306,109 A | 4/1994 | Kreuzer et al. | |
| 5,319,816 A | 6/1994 | Ruehl | |
| 5,344,169 A | 9/1994 | Pryor et al. | |
| 5,366,191 A | 11/1994 | Bekanich | |
| 5,377,371 A | 1/1995 | Foster | |
| 5,396,673 A | 3/1995 | Foster | |
| 5,398,359 A | 3/1995 | Foster | |
| 5,400,995 A | 3/1995 | Boyd | |
| 5,618,090 A | 4/1997 | Montague et al. | |
| 5,647,491 A | 7/1997 | Foster et al. | |
| 5,820,086 A | 10/1998 | Hoftman et al. | |
| 5,826,847 A | 10/1998 | Warner et al. | |
| 5,898,961 A | 5/1999 | Ambach et al. | |
| 5,987,670 A | 11/1999 | Sims et al. | |
| 6,073,285 A | 6/2000 | Ambach et al. | |
| 6,089,518 A | 7/2000 | Nilsson | |
| 6,095,468 A | 8/2000 | Chirico et al. | |
| 6,179,260 B1 | 1/2001 | Ohanian | |
| 6,375,133 B1 | 4/2002 | Morrow | |
| 6,434,329 B1 | 8/2002 | Dube et al. | |
| 6,471,363 B1 | 10/2002 | Howell et al. | |
| 6,585,206 B2 | 7/2003 | Metz et al. | |
| 6,619,599 B2 | 9/2003 | Elliott et al. | |
| 6,704,956 B2 | 3/2004 | Riley et al. | |
| 6,899,442 B2 | 5/2005 | Howell et al. | |
| 6,966,086 B2 | 11/2005 | Metz et al. | |
| 7,008,269 B2 | 3/2006 | Riley et al. | |
| 7,065,811 B2 | 6/2006 | Newkirk et al. | |
| 7,065,812 B2 | 6/2006 | Newkirk et al. | |
| 7,216,382 B2 | 5/2007 | Newkirk et al. | |
| 7,314,200 B2 * | 1/2008 | Bally et al. | 248/276.1 |
| 7,789,361 B2 * | 9/2010 | Bally et al. | 248/229.2 |
| 7,921,489 B2 * | 4/2011 | Newkirk et al. | 5/600 |
| 2002/0047075 A1 | 4/2002 | Metz et al. | |
| 2004/0199996 A1 | 10/2004 | Newkirk et al. | |
| 2005/0000019 A1 | 1/2005 | Newkirk et al. | |
| 2005/0253034 A1 | 11/2005 | Bally et al. | |
| 2006/0038098 A1 | 2/2006 | Metz et al. | |
| 2006/0043244 A1 | 3/2006 | Graham et al. | |
| 2006/0207026 A1 | 9/2006 | Newkirk et al. | |
| 2006/0242763 A1 | 11/2006 | Graham et al. | |

FOREIGN PATENT DOCUMENTS

| | | |
|---|---|---|
| WO | WO 2005/037163 A2 | 4/2005 |
| WO | WO 2005/037165 A2 | 4/2005 |

OTHER PUBLICATIONS

Gray Eggleston's IV-Ease Transportation System—www.abc.net.au/newinventors/txt/s1150413.htm, date unknown, 2 pages.

Modular Services Company's Pump Star™—The Headwall Company brochure dated 2005.

Trumpf Kreuzer Medizin Systeme GmbH & Co. KG—IMEC System—Technical Data dated Apr. 7, 2005.

Innovative Medical Designs' Advanced IV Transport—Data Sheet dated Jun. 14, 2005.

International Preliminary Report on Patentability and Written Opinion mailed Apr. 9, 2009 (8 pages).

* cited by examiner

MEDICAL EQUIPMENT TRANSFER ARRANGEMENT

CROSS-REFERENCE TO RELATED APPLICATIONS

This application claims the benefit of U.S. Provisional Application Nos. 60/847,838, filed Sep. 28, 2006, and 60/937,398, filed Jun. 27, 2007.

FIELD OF THE INVENTION

This invention generally relates to an arrangement for transferring medical equipment supported on a post assembly between two support structures.

BACKGROUND OF THE INVENTION

Patients in a hospital setting often require a number of pieces of medical equipment for their care. Such medical equipment may include intravenous-related devices, monitors for tracking vital signs of the patient, oxygen tanks, etc. This equipment is necessarily connected directly to the patient, and is thus typically supported on an upright post-type assembly kept near the patient, and which travels along with the patient as the patient is transported between various areas of care in the hospital. These types of post assemblies are sometimes provided as freestanding wheeled units, and thus transporting the patient can require multiple persons, one to manipulate the patient support, and another to manipulate the post assembly carrying the associated medical equipment.

In view of the above, post assemblies which mount directly to the patient support have been developed, which are easier to handle since same travel along with the patient support. Further, in some settings, such as an operating room, intensive care area or patient room, it is often desirable to support the equipment associated with a particular patient on a stable support structure, such as an arrangement which is mounted directly to a wall, floor or ceiling of the room or area. As the patient is moved between different areas in the hospital, for example for procedures or testing, it is necessary to transfer the equipment associated with the patient between various support structures. Accordingly, there is a need for ease in transfer of a post assembly of the type described above between these support structures.

SUMMARY OF THE INVENTION

In accordance with the present invention, there is provided a positioning arm which is utilized to transfer an upright post assembly between two support structures. The positioning arm at one end is attached to a first support structure, such as a support column, service head, equipment boom or wall, and at the other end supports an upright post assembly which carries medical equipment thereon. Such equipment may be IV-related devices, pumps, patient monitors or the like which are typically attached to the patient. The second support structure may be a patient transfer device, such as a patient support or bed, surgical table, stretcher or wheelchair. The second support structure may also be a wheeled support stand which is freestanding or movable independently of any other support structure, for example along with the patient. The positioning arm is articulated and movable in a generally horizontal plane, and is thus easily manipulatable and usable to vertically align the lower end or base of the post assembly with a receiver provided on the support to which the post is to be transferred. The positioning arm is thus also easy to position for receipt of the post assembly when same is being transferred from a support to the positioning arm.

In one embodiment, the positioning arm is used to transfer the post assembly to or from a patient support, for example, a patient bed. A receiver assembly is firmly attached to the frame of the patient support, which receiver assembly is configured to receive the lower end of the post assembly. Many patient supports are motorized or manually-manipulatable to allow vertical height adjustment thereof, and this embodiment of the invention accordingly utilizes this feature of the patient support in order to place the post assembly at the proper vertical height for transfer from the patient support to the other support or vice versa.

In another embodiment, a freestanding cart is provided which supports the post assembly. The cart is configured to accept the post assembly, when same is supported on a vertically-adjustable patient support or bed, to permit the patient to ambulate with their associated equipment. This embodiment also utilizes the vertical motion of the patient support to place the post assembly at the proper vertical height to permit transfer from the patient support to the cart, and vice-versa.

In accordance with another embodiment, a post assembly is provided which is self-actuable to allow height adjustment of the post assembly for proper positioning of the assembly for transfer between supports, without the need for utilizing the height adjustment feature of the patient support.

Other objects and purposes of the invention will be apparent to persons familiar with arrangements of this general type upon reading the following description and inspecting the accompanying drawings.

Figure 1:
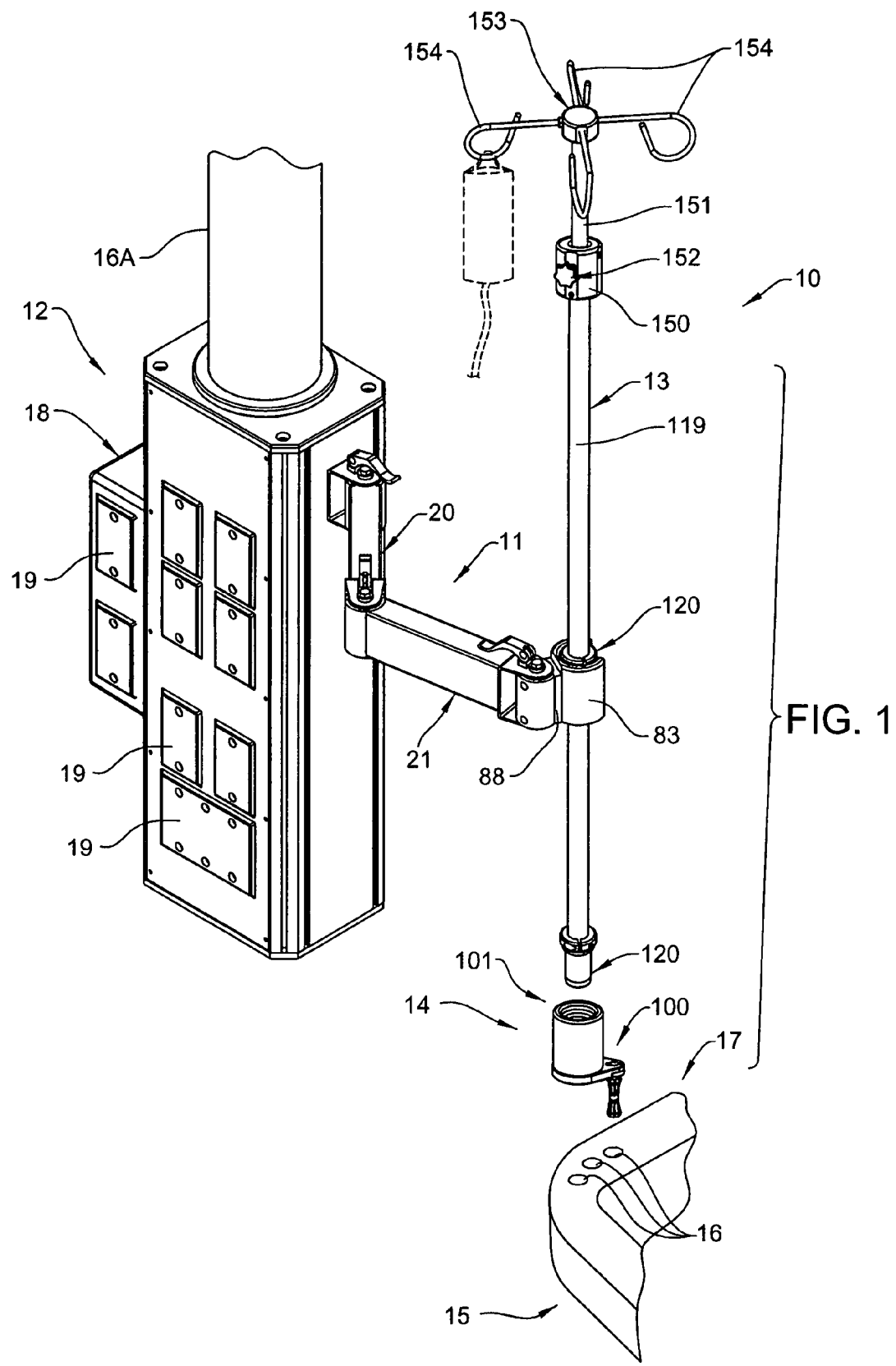
FIG. 1 is an exploded perspective view of the equipment transfer arrangement according to the invention.

Certain terminology will be used in the following description for convenience in reference only, and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the arrangement and designated parts thereof. The word "frontwardly" with respect to the cart arrangement will refer to the side of the cart on which the post assembly is supported, and the word "rearwardly" will refer to the side of the cart opposite the post assembly. Said terminology will include the words specifically mentioned, derivatives thereof, and words of similar import.

DETAILED DESCRIPTION

FIG. 1 illustrates a medical equipment transfer arrangement 10, generally including a positioning arm 11 which is supported on a support 12. Support 12 may be any permanent-type or stationary structure, such as a wall, floor ceiling or wall-mounted column. For the purpose of illustration, support 12 is a service head or boom which may be wall or ceiling-mounted. The outermost free end of positioning arm 11 supports a generally upright support structure, which in the illustrated embodiment is a pole or post assembly 13 which supports medical equipment. Such medical equipment may constitute infusion pumps, IV fluid bags (shown in dotted lines in FIG. 1) or other IV-related equipment. It will be appreciated that post assembly 13 may alternatively support other types of medical equipment such as patient monitors, oxygen tanks, etc. When desirable or necessary, the post assembly 13 is transferred by the positioning arm 11 from the service head 12 to a transfer device 17. Device 17 may be any type of transfer device, such as a patient bed, stretcher, wheelchair, transfer cart or surgical table. In the illustrated embodiment, device 17 is a patient support or bed. A bed mounting assembly 14 provided on the patient support 17 includes a frame 15, which frame 15 defines therein one or more upwardly-opening mounting holes 16 therein. These mounting holes 16 are typically of differing dimensions or diameters, so as to accommodate various types of equipment.

It will be appreciated that the support or service head 12 shown in FIG. 1 is conventional, and is a commercially available product sold by the Assignee hereof. The support 12 will accordingly be only briefly described herein. Support 12 is a ceiling-mounted arrangement configured so as to allow vertical and/or horizontal positioning of the arm 11. Specifically, the support 12 includes an upper support element, boom or down tube 16A with an upper end rotatably supported on a ceiling of a care area or room, for example an intensive care unit. Support or service head 12 additionally includes a lower part 18 having gas, data and/or electrical outlets or connections 19 for supporting various types of medical equipment. Service head 12 may also incorporate shelves for supporting equipment directly thereon.

Figure 2:
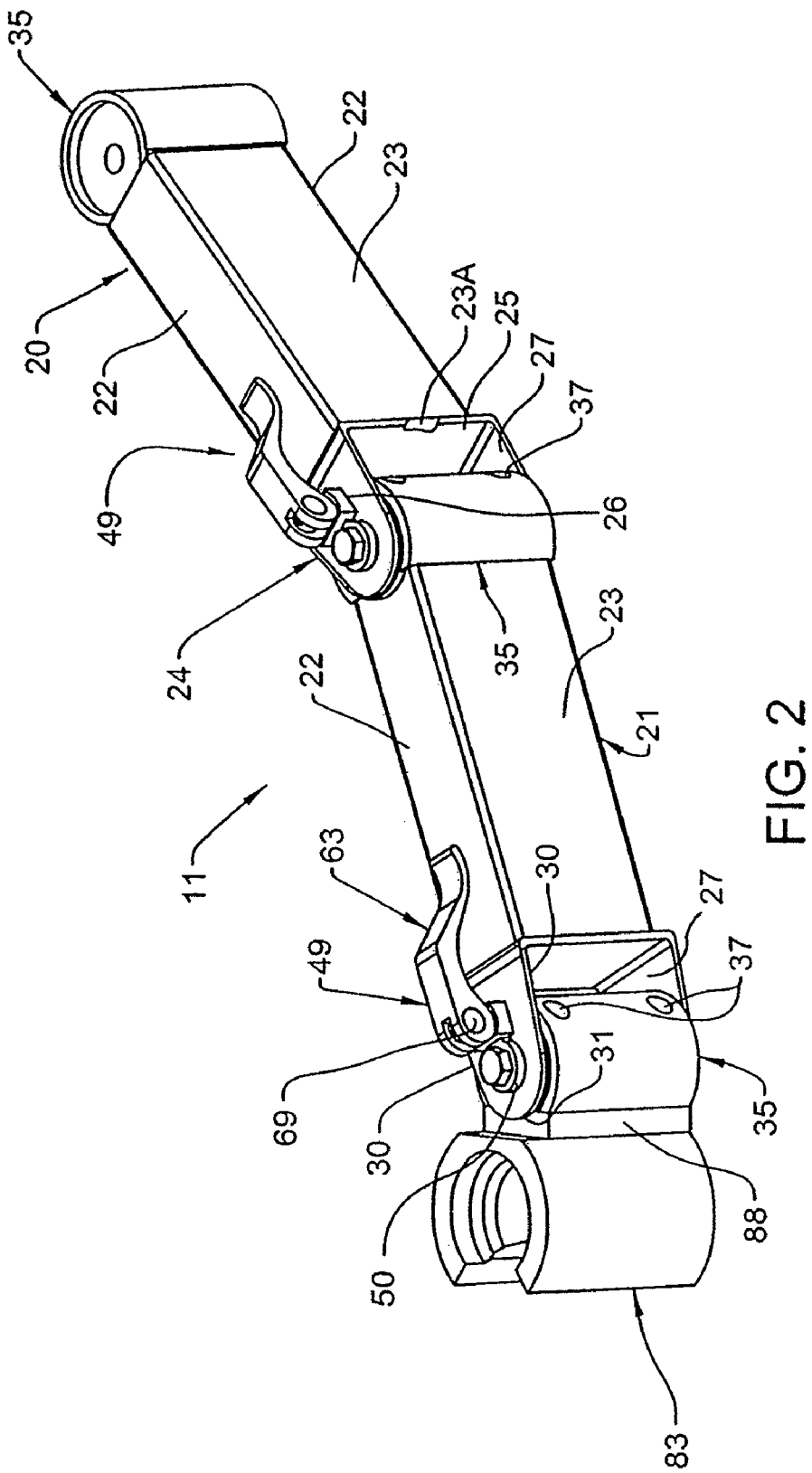
FIG. 2 is an enlarged perspective view of the positioning arm.
Figure 3:
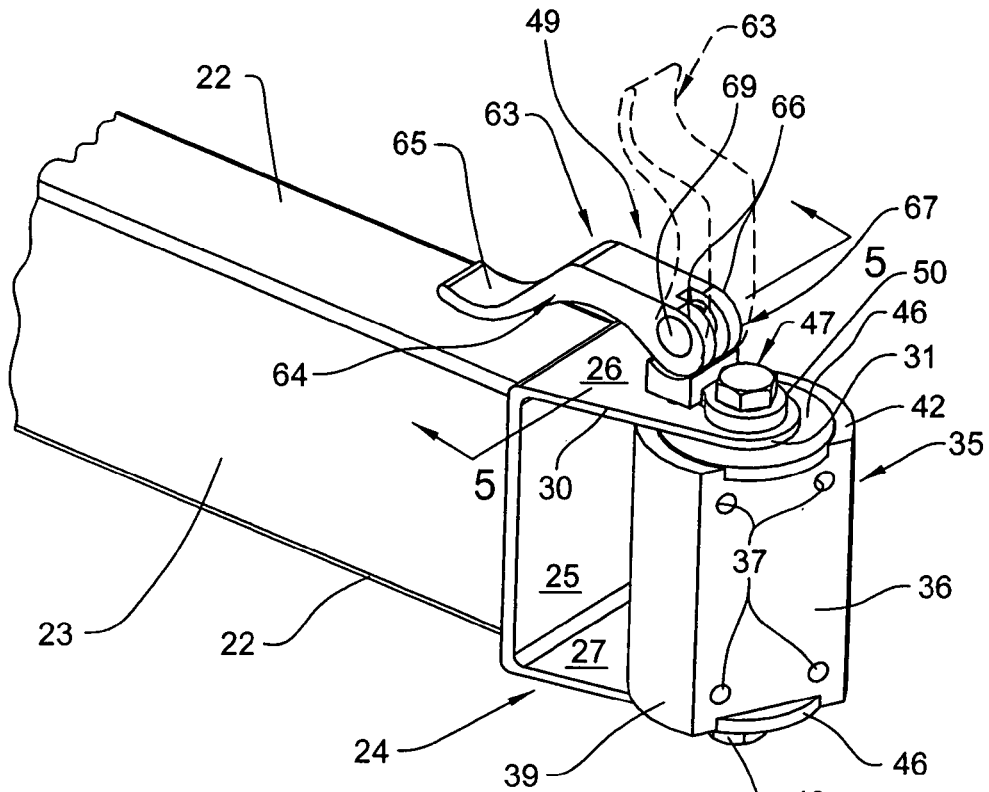
FIG. 3 is an enlarged fragmentary and perspective view of one arm segment of the positioning arm.

Turning now to positioning arm 11, and referring to FIGS. 1-3, same includes an inner arm section or link 20 ("inner" referring to the arm link closest to service head 12) which is connected at its outer end to an outer arm link or arm section 21. It should be noted that the illustrated embodiment incorporates two arm links as discussed above. However, it will be appreciated that the arrangement according to the invention may of course include additional arm links if a greater overall arm mobility or reach is necessary or desirable.

Figure 5:
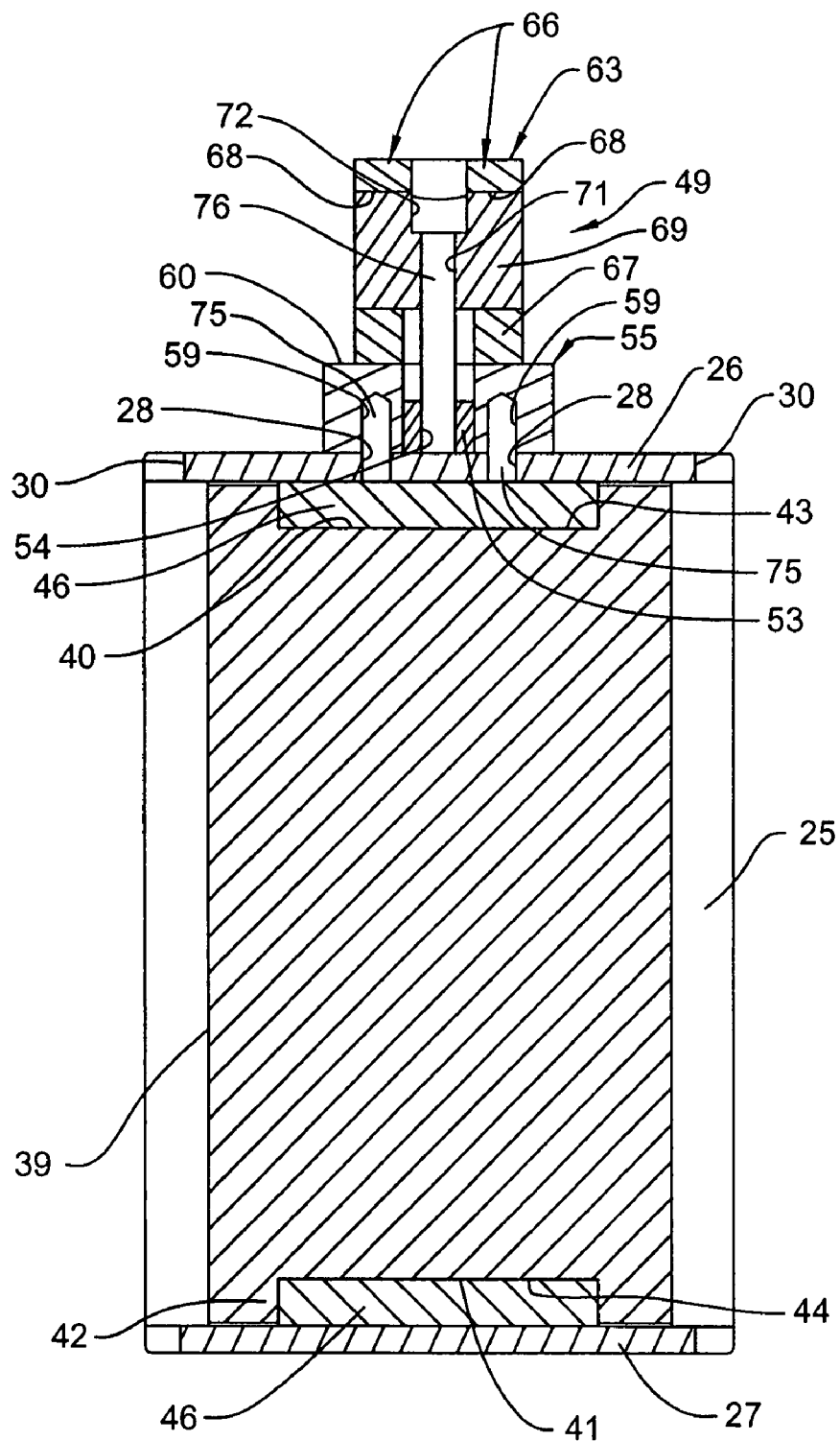
FIG. 5 is an enlarged cross-sectional view of the clamping arrangement of the positioning arm, taken generally along line 5-5 in FIG. 3.

Arm links 20 and 21 are of an identical construction, and thus the same reference numbers will be utilized to refer to the same or similar components. Each arm link 20 and 21 is of generally rectangular cross-sectional construction. However, it will be appreciated that the cross-sectional shape of the link may include additional geometric shapes if necessary or desirable. In the illustrated embodiment, arm links 20 and 21 are of a solid construction and include generally parallel, spaced-apart and horizontal top and bottom surfaces 22 and generally parallel, spaced-apart and upright side surfaces 23 which extend between and interconnect the top and bottom surfaces 22. A pair of upright end surfaces 23A (only one of which is shown in FIG. 2) are oriented at the respective opposite ends of the respective arm link and define the terminal ends thereof. The outer end of inner arm link 20 is interconnected to the inner end of outer arm link 21 by means of a clevis 24. Clevis 24 includes a generally upright wall 25 which is fixed to the outer end surface 23A of inner arm link 20 by a suitable fastening method, a top wall 26 cantilevered sidewardly from an upper edge of upright wall 25, and a bottom wall 27 cantilevered sidewardly from a lower edge of upright wall 25. Top and bottom walls 26 and 27 are generally parallel to one another and are generally perpendicular relative to upright wall 25. As shown in FIG. 5, top wall 26 defines therein a pair of sidewardly-spaced through-holes or openings 28 approximately mid-way along the length of top wall 26. Further, in the illustrated embodiment, the side edges 30 of each of top and bottom walls 26 and 27 of clevis 24 diverge towards one another as same project away from upright wall 25, and join at a generally rounded edge 31.

Figure 4:
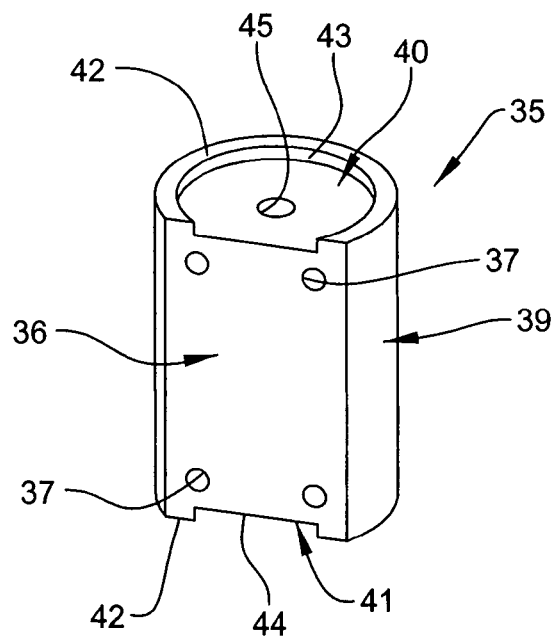
FIG. 4 is an enlarged perspective view of the pivot bracket.

Referring to FIGS. 2-4, a pivot bracket 35 which is generally cylindrical in shape, and in the illustrated embodiment hollow, is pivotably mounted between top and bottom walls 26 and 27 of clevis 24. Pivot bracket 35 in the illustrated embodiment is a solid component, and includes on one side thereof a flat upright fastening surface 36 which is fixed to innermost end surface 23A of outer arm 21 via suitable fasteners. In this regard, the fasteners extend through openings or bores 37 which extend completely through bracket 35 and open through both fastening surface 36 and the opposite side of bracket 35. These fasteners extend through the openings 37 and into corresponding openings (not shown) provided in end surface 23A of outer arm 21. The pivot bracket 35 is essentially defined by an upright and semi-circular outer surface 39 which is joined at opposite upright edges thereof to opposite upright side edges of fastening surface 36. Bracket 35 further includes top and bottom surfaces 40 and 41 which are spaced vertically downwardly and upwardly, respectively, from upper and lower semi-circular edges or flanges 42 of bracket 35 so as to define respective upwardly and downwardly opening recesses 43 and 44. A hole 45 extends vertically through bracket 35 and opens through top and bottom surfaces 40 and 41.

A pair of annular bearing plates 46 are disposed in the respective recesses 43 and 44, central openings or holes of which are aligned with the opening 45 of bracket 35. A pivot bolt 47 extends downwardly through an opening (not shown) defined in top wall 26 of clevis 24, which opening is defined outwardly of openings 28 and inwardly of edge 31, through upper bearing plate 46, through opening 45 in pivot bracket 35, through lower bearing plate 46, and through a corresponding opening (not shown) defined in bottom wall 27 of clevis 24. It will be appreciated that the openings defined in top and bottom walls 26 and 27 of clevis 24 which receive bolt 47 are vertically aligned with one another. A nut 48 is then secured to lower end of pivot bolt 47.

Figure 8:
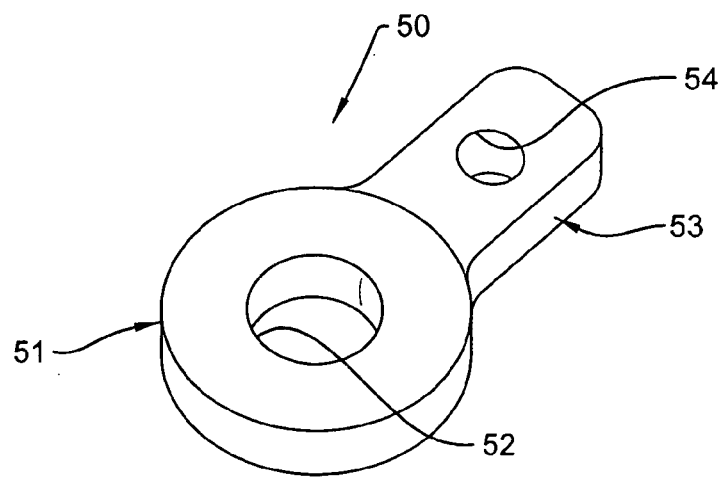
FIG. 8 is an enlarged perspective view of the positioning washer of the clamping arrangement.

Arm 11 additionally includes an arm-clamping assembly 49 disposed at the outer end of arm segment 20, which cooperates with clevis 24 and pivot bracket 35. With reference to FIG. 8, clamping assembly 49 includes a positioning washer 50 having an annular section 51 defining a centrally-oriented opening 52, and a reduced-width stem section 53 defining therein a threaded opening 54.

Figure 6:
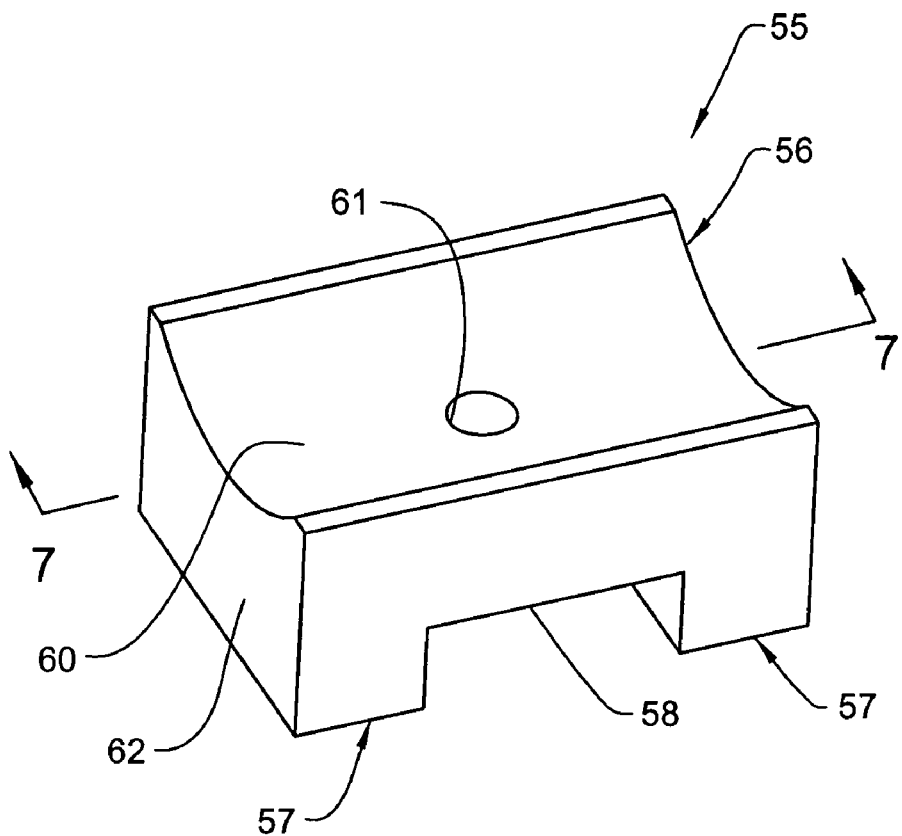
FIG. 6 is an enlarged perspective view of the pusher plate of the clamping arrangement.
Figure 7:
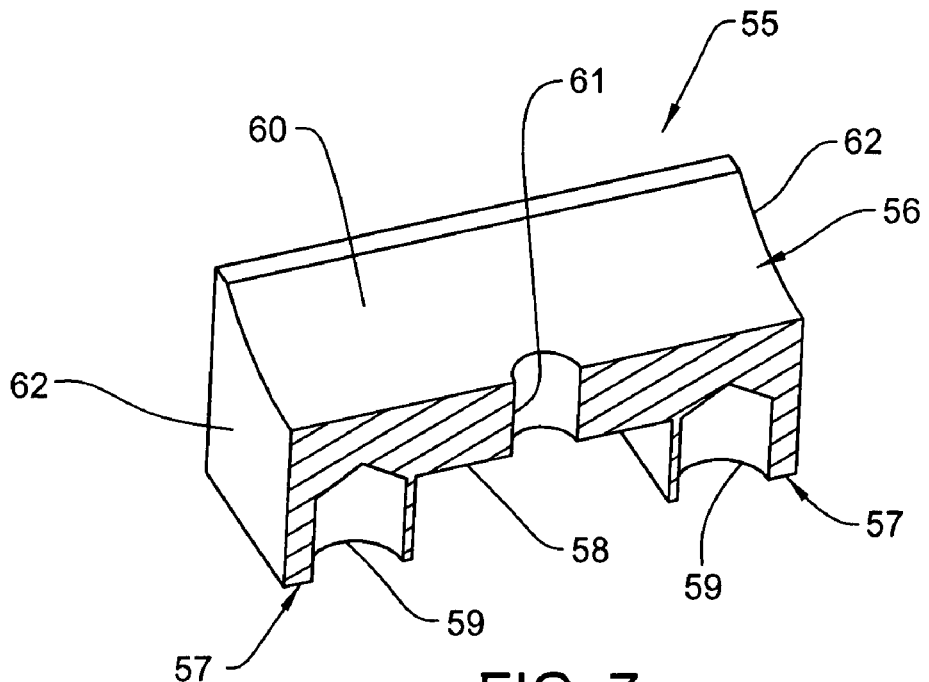
FIG. 7 is a cross-sectional view of the pusher plate, taken generally along line 7-7 in FIG. 6.

Clamping assembly 49 further includes a pusher plate 55 as shown in FIGS. 6 and 7. Pusher plate 55 has an upper generally horizontally oriented section 56, and a pair of generally upright legs 57 which project downwardly from opposite sides of said upper section 56. Legs 57 are laterally-spaced from one another so as to define therebetween a channel 58 which extends throughout the transverse dimension of the pusher plate 55. Channel 58 is of a size similar to, but somewhat larger than, the transverse width of stem section 53 of positioning washer 50. Each leg 57 defines therein a downwardly-opening hole 59 which projects upwardly into the material of leg 57 and terminates adjacent upper section 56. The upper section 56 of pusher plate 55 defines an upwardly-opening arcuate surface 60, and an opening 61 which projects downwardly through surface 60 and completely through the material of upper section 56 between legs 57. Surface 60 joins to generally upright side surfaces 62 of legs 57 along opposite transverse edges thereof.

Figure 9:
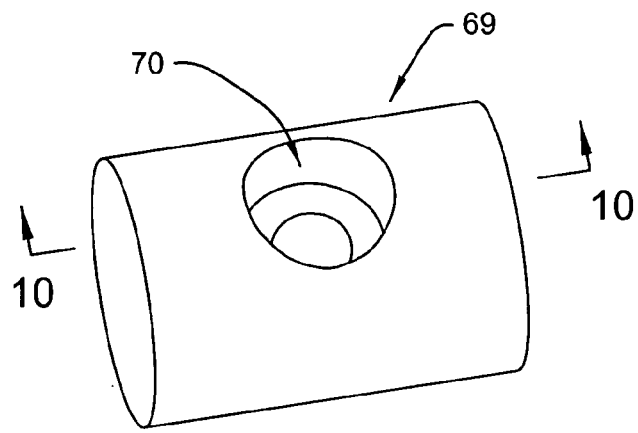
FIG. 9 is an enlarged perspective view of the pivot member of the clamping arrangement.
Figure 10:
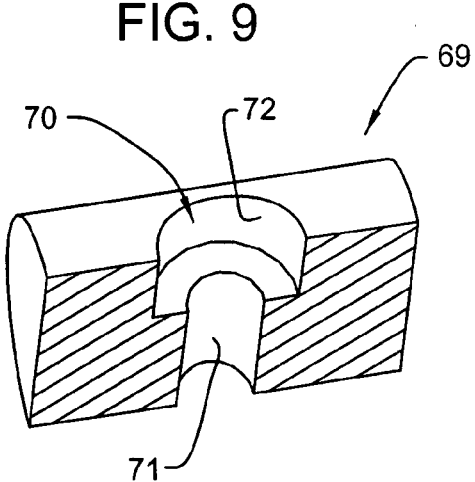
FIG. 10 is a cross-sectional view of the pivot member, taken generally along line 10-10 in FIG. 9.

A clamping arm 63 is incorporated into clamping assembly 49. Clamping arm 63 includes an inner free end which defines a handle 64 for manipulating arm 63. For ease in use, handle 64 includes a shallow and concave area 65 which provides a gripping surface for the user. The outer end of clamping arm 63 is of a forked construction, the identical forks 66 of which each define a cam 67 thereon. Each fork 66 defines therein a horizontally oriented opening 68, through which openings 68 a pivot member 69 is disposed. As best shown in FIG. 5, the openings 68 are axially aligned with one another, but are offset from a central horizontal axis of outer end of clamping arm 63. With reference to FIGS. 9 and 10, pivot member 69 is generally cylindrical in shape, and defines therein a generally upright through bore 70. Bore 70 includes a lower bore portion 71 and an upper bore portion 72 of a greater diameter than lower bore portion 71, such that the cross-sectional configuration of bore 70 is generally T-shaped.

The components of clamping assembly 49 are assembled as follows. Prior to insertion of pivot bolt 47 into pivot bracket 35 as discussed above, positioning washer 50 is positioned on top wall 26 of clevis 24, so that opening 52 thereof is aligned with the opening defined at the free end of top wall 26. Pivot bolt 47 is then inserted downwardly through pivot bracket 35 as discussed above, with the head of pivot bolt 47 resting atop annular section 51 of washer 50. A pair of brake pins 75 are inserted upwardly into the respective openings 59 of pusher plate 55. Pusher plate 55 is then positioned atop stem section 53 of washer 50, with stem section 53 disposed within channel 58 of pusher plate 55, wherein the lower ends of the pins 75 extend through the respective openings 28 of top wall 26 of clevis 24. The clamping arm 63 with pivot member 69 inserted therein is then positioned atop pusher plate 55, so that the cams 67 are positioned atop and in contacting engagement with arcuate upper surface 60 thereof. A threaded bolt or screw 76 is then inserted downwardly into bore 70 of pivot member 69, through bore sections 72 and 71 thereof, through opening 61 of pusher plate 55, and into threaded opening 54 positioning washer 50. It will be appreciated that the diameter of opening 61 of pusher plate 55 is sized larger than the diameter of bolt 76 and, so as to allow vertical movement of pusher plate 55 relative to bolt 76. As discussed below, the bolt 76 is adjustable to provide the desired amount of clamping force.

With respect to the opposite or inner end of arm segment 20 adjacent support 12, a pivot bracket (FIG. 2) identical to pivot bracket 35 is mounted thereon, wherein a flat wall thereof is fixed to innermost end surface 23A of arm segment 20. Service head 12 mounts, on an upright side wall of lower part 18 thereof, a clevis identical to clevis 24 which receives pivot bracket 35 located on the inner end of arm segment 20. A clamping assembly 49 is also provided on clevis 24 secured to service head 12.

The outer end of arm segment 21 mounts thereon a clevis identical to clevis 24, as well as a pivot bracket identical to pivot bracket 35. A clamping assembly 49 is also provided on clevis 24 mounted on the outer end of arm segment 21 in the manner discussed above.

Figure 11:
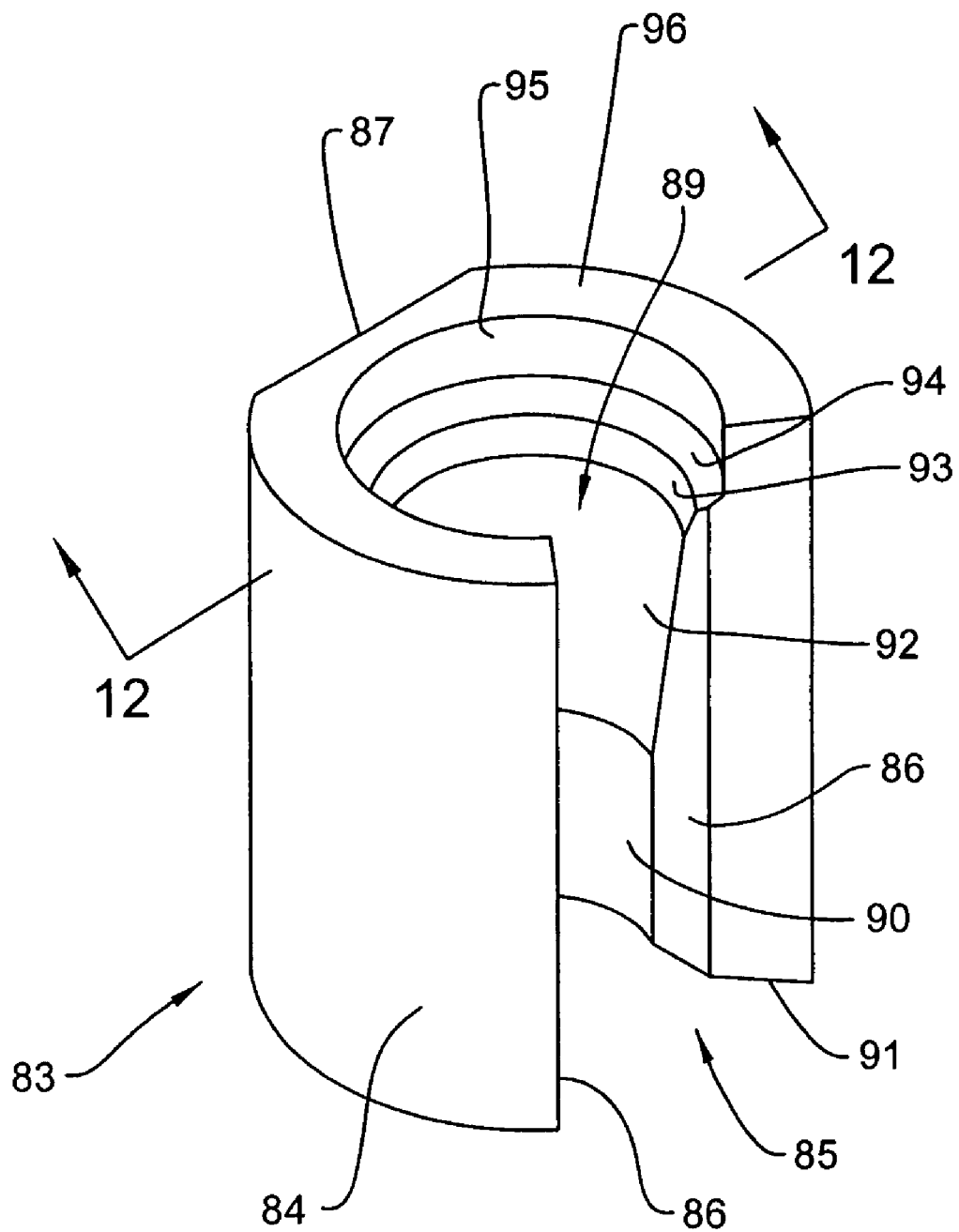
FIG. 11 is an enlarged perspective view of the upper receiver of the positioning arm.
Figure 12:
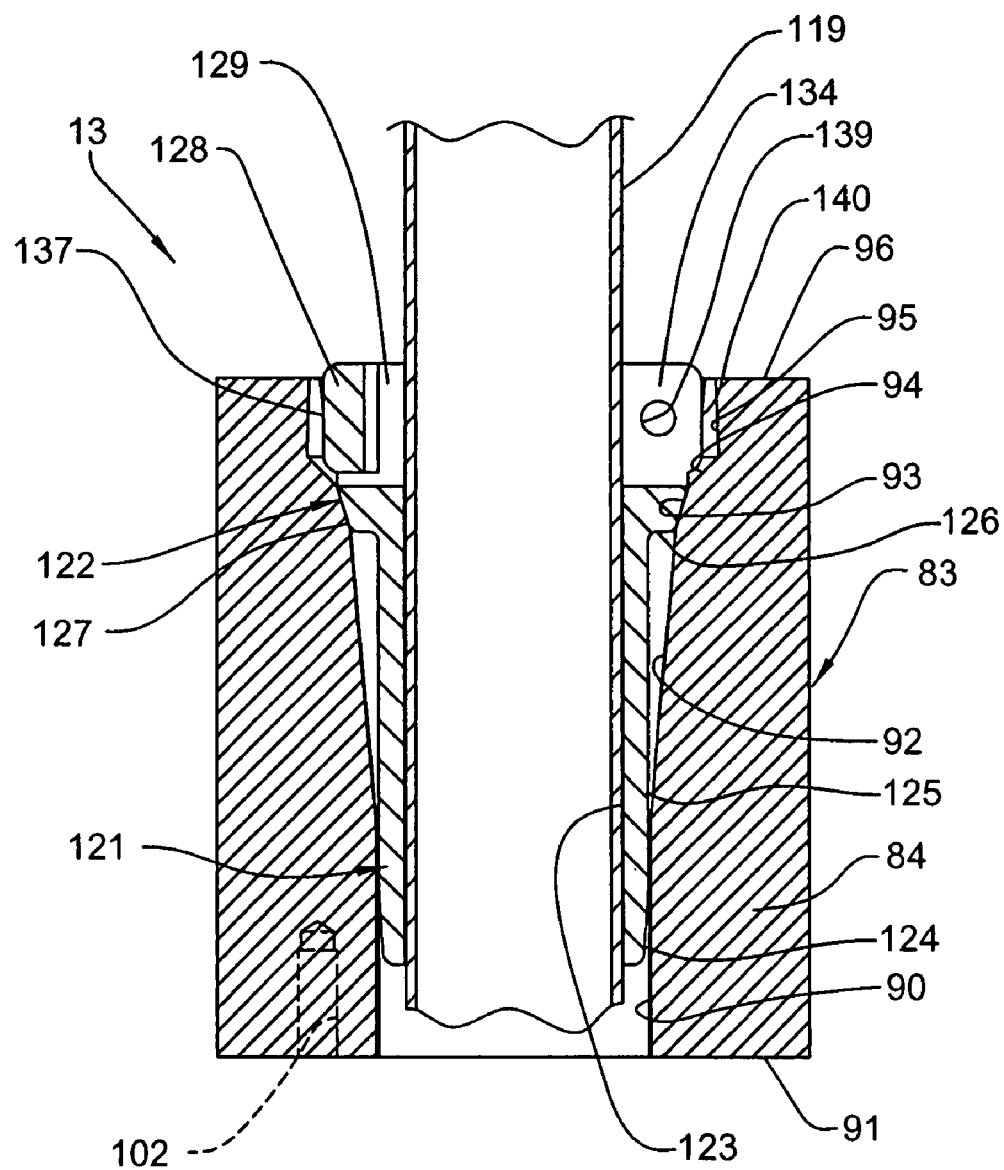
FIG. 12 is a cross-sectional view of the upper receiver, taken generally along line 12-12 in FIG. 11, and additionally including the post sleeve and post disposed in the upper receiver.

Referring to FIGS. 1, 11 and 12, an upper receiver 83 is mounted at the outer end of outer arm segment 21. Receiver 83 is generally sleeve-shaped and is defined by an upright wall 84 defining a vertical slit or slot 85 therein which extends completely vertically through wall 84. This slit 85 is defined by a pair of upright and horizontally-spaced apart edges 86 of wall 84. Wall 84 is generally cylindrically-shaped as same projects away from edges 86, and is joined to a flat wall 87 located diametrically opposite slit 85. Wall 87 of receiver 83 is joined to flat wall 36 of the respective pivot bracket 35 via a spacer element 88 and suitable fasteners.

Wall 84 of upper receiver 83 additionally defines therein a through bore 89, as best illustrated in FIGS. 11 and 12. Bore 89 includes a lowermost cylindrical bore portion 90 of the smallest bore diameter, which opens downwardly through a lowermost and generally horizontal surface 91 of wall 84. An intermediate portion 92 of bore 89 extends upwardly from lowermost portion 90, the diameter of which diverges outwardly as the bore portion 92 projects upwardly. An upper intermediate bore portion 93 extends upwardly from intermediate bore portion 92 of bore 89, and diverges outwardly at a greater angle than intermediate bore portion 92 as same projects upwardly. Upper intermediate bore portion 93 defines an angled support ridge which cooperates with post assembly 13 as discussed further below. Bore 89 additionally includes an upper tapered bore portion 94 extending upwardly from bore portion 93, which bore portion 94 diverges outwardly at a greater angle than bore portion 93 as same projects upwardly. Lastly, bore 89 includes an uppermost bore portion 95 which extends upwardly from bore portion 94 and opens outwardly through an uppermost and generally horizontal surface 96 of wall 84. Uppermost bore portion 95 is of a generally cylindrical configuration, and defines the largest bore diameter of bore 89.

Figure 13:
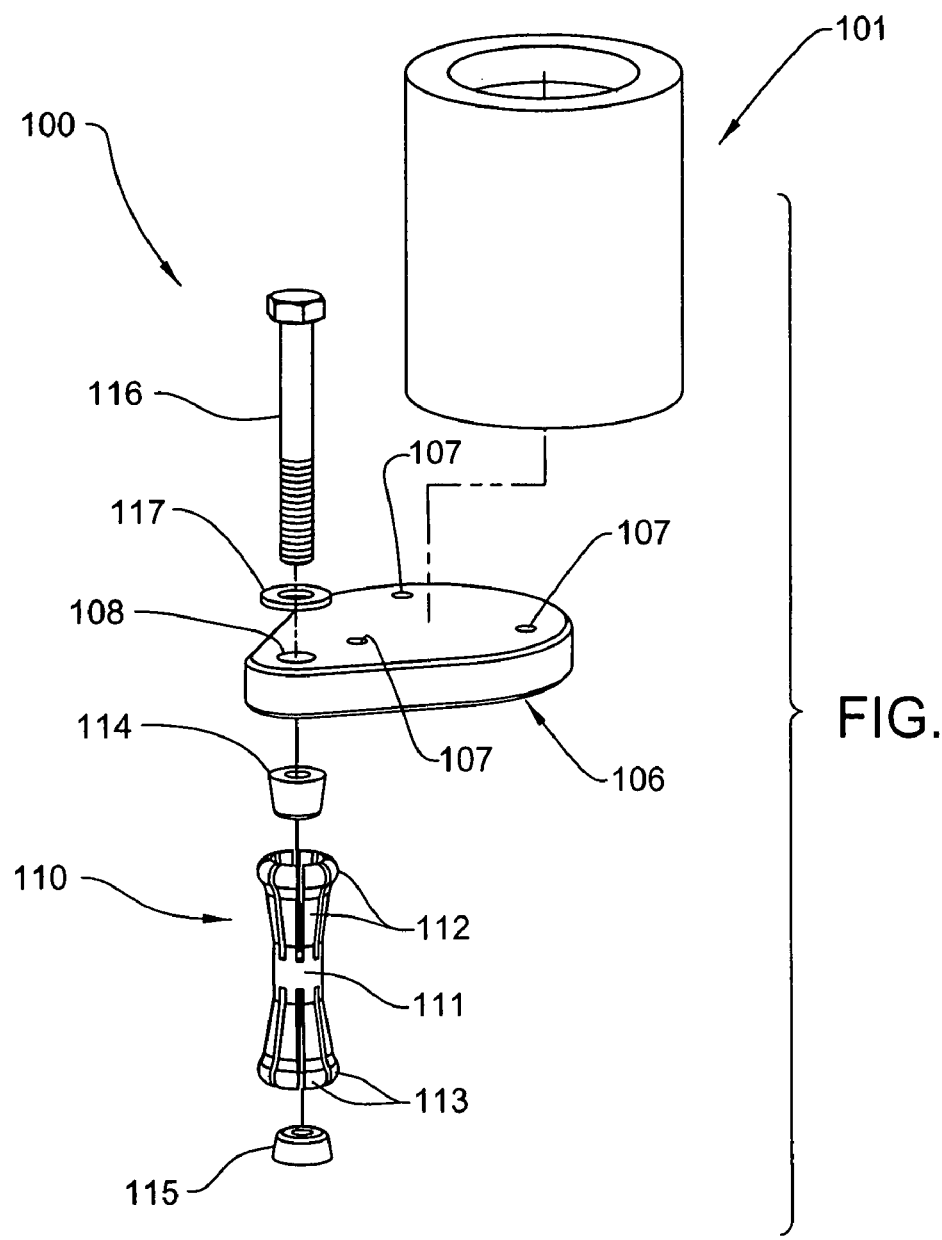
FIG. 13 is an enlarged exploded perspective view of the lower receiver assembly.

As shown in FIGS. 1 and 13, mounting assembly 14 includes a lower receiver assembly 100 for mounting on frame 15 of the patient support or bed. Assembly 100 includes a lower receiver 101 which is identical to upper receiver 83 provided on outer arm segment 21, except that lower receiver 101 is not vertically split (as is receiver 83 at 85) and does not include a flat wall (as does receiver 83 at 87). Accordingly, lower receiver 101 is fully cylindrical in shape, and the interior thereof corresponds to the cross-sectional shape of upper receiver 83 as illustrated in FIG. 12. A further difference between upper receiver 83 and lower receiver 101 is that lower receiver 101 includes a plurality, and here three, of threaded openings 102 (one of which is shown in dotted lines in FIG. 12) for receiving fasteners as discussed below, which openings 102 open downwardly through a lowermost surface of receiver 101.

Lower receiver assembly 100 also includes a generally flat mounting plate 106 which in the illustrated embodiment has the general shape of a tear-drop. Mounting plate 106 defines therein a plurality, and here three, of mounting holes 107. Mounting holes 107 are located in positions corresponding to openings 102 of lower receiver 101, and fasteners are inserted upwardly through holes 107 and into openings 102 to fix mounting plate 106 to lower receiver 101. A further hole 108 is provided in mounting plate 106 at the narrowest portion thereof.

With continued reference to FIG. 13, lower receiver assembly 100 includes a collet 110 having a ring-like intermediate portion 111. A plurality of fingers 112 are cantilevered upwardly from intermediate portion 111 and are spaced-apart from one another about the circumference of portion 111. Further, a plurality of circumferentially-spaced fingers 113 are cantilevered downwardly from intermediate portion 111. Upper and lower annular and interiorly-threaded wedges 114 and 115 are sized to fit within openings of collet 110 as defined by the upper and lower fingers 112 and 113. A threaded bolt 116 and washer 117 fix the assembly together as discussed below. The opening of collet 110 defined by fingers 112 and the outer side surface of upper wedge 114, and the opening of collet 110 defined by fingers 113 and the outer side surface of lower wedge 115, have corresponding tapers. In the illustrated embodiment, the matching taper angles of the opening in collet 110 defined by upper fingers 112 and upper wedge 114 are steeper or greater than the matching taper angles of the opening in collet 110 defined by lower fingers 113 and lower wedge 115.

Turning now to post assembly 13, and with reference to FIGS. 1, 12, 14 and 15, same includes an elongate and upright post 119. Post 119 mounts thereon a pair of upper and lower post sleeves 120 which are identical to one another, and only one of such sleeves 120 is accordingly described in detail herein. Sleeve 120 includes an elongate and generally tubular lower portion 121 and a generally annular upper portion 122 provided atop and fixed to lower portion 121. Sleeve 120 defines a through bore 123 which extends completely through the vertical extent of sleeve 120, and in the illustrated embodiment has a constant diameter throughout.

Figure 14:
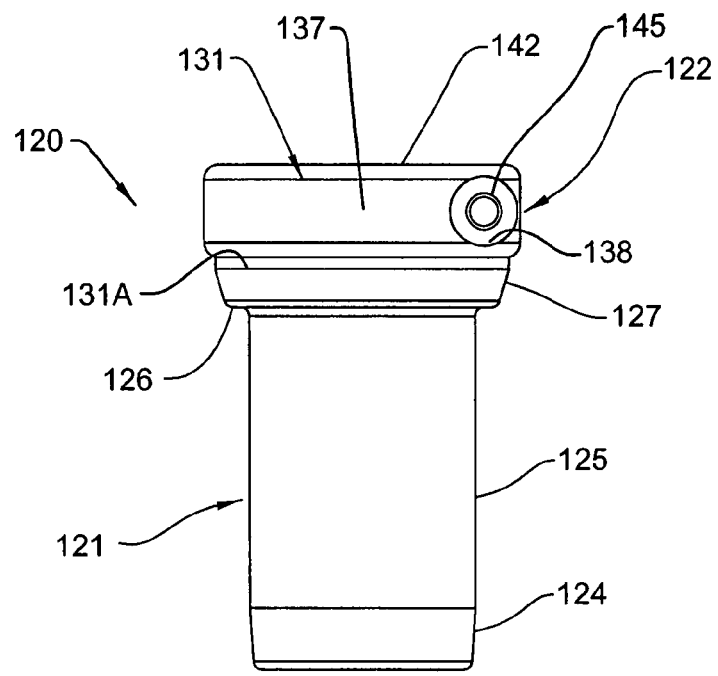
FIG. 14 is an enlarged side view of the post sleeve.

Referring to the lower portion 121 of sleeve 120, and with reference to FIGS. 12 and 14, portion 121 defines an outer surface having a lowermost section 124 which diverges slightly outwardly as same projects upwardly, and a generally cylindrical intermediate section 125 of a constant outer diameter which extends upwardly from lowermost section 124. Lower portion 121 additionally defines a step or shoulder 126 which is joined to intermediate section 125, and a tapered section 127 which diverges outwardly as same projects upwardly away from shoulder 126. Tapered section 127 is configured in a manner complementary to upper intermediate portion 93 of arm receiver 83.

Figure 15:
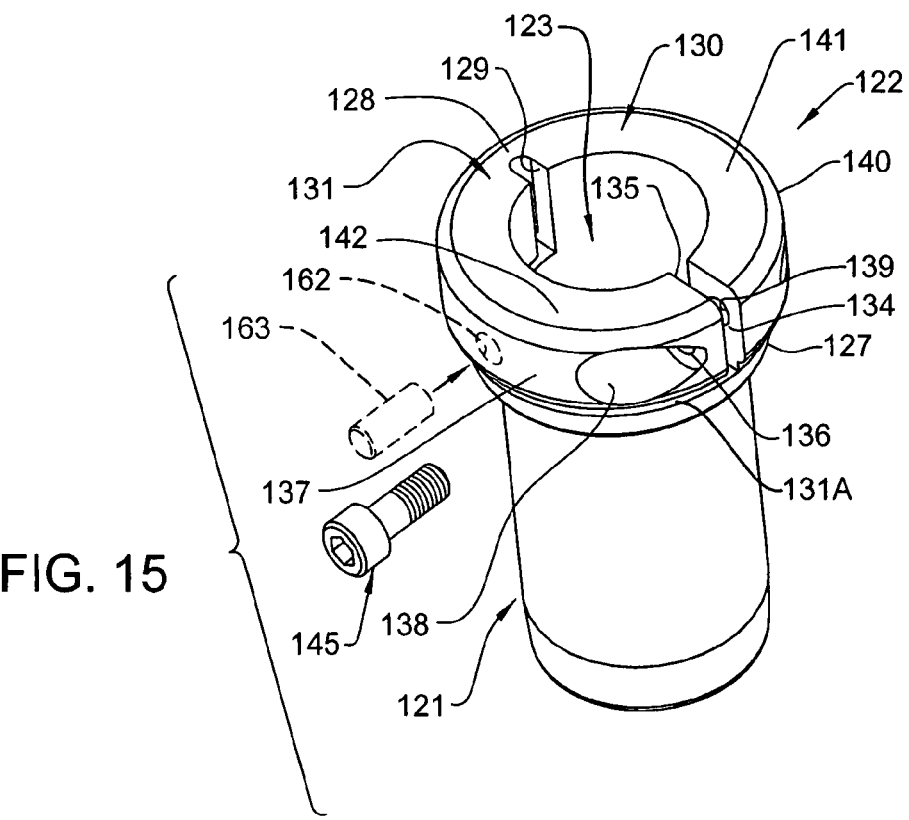
FIG. 15 is an enlarged exploded perspective view of the post sleeve.

In the illustrated embodiment, upper annular portion 122 is of a split construction. More specifically, and as best shown in FIG. 15, upper portion 122 is defined by two half-ring members 130 and 131. Half-ring member 130 is fully joined at its lower end thereof to tapered section 127 of lower portion 121. The opposite ring-member 131 is separated and spaced upwardly from tapered section 127 along the majority of its circumferential extent (see space 131A in FIGS. 14 and 15), and is joined to one edge of ring-member 130 at a connection area 128. Connection area 128 is recessed at 129, and defines a pivot area of ring member 131 relative to the opposite ring member 130. The respective ring members 130 and 131 define opposed end surfaces 134 and 135, which end surface 135 is disposed at the free end of ring member 131.

In addition, ring member 131 defines therein an opening 136 which opens sidewardly through a generally upright and cylindrical outer side surface 137 of member 131 through a widened access opening 138 which communicates with, and constitutes an extension of, opening 136. The inner end of opening 136 opens through surface 135. The opposite ring member 130 defines therein a threaded opening 139 which is aligned with opening 136, and opens sidewardly through surface 134. Ring member 130, similar to ring member 131, defines a generally upright and cylindrical outer side surface 140. Further, each of ring members 130 and 131 define respective upper and generally horizontally oriented and semi-circular surfaces 141 and 142, which are generally coplanar with one another.

Post 119 is disposed within through bore 123 of sleeve 120, and ring member 131, being movable relative to ring member 130, effectively operates as a clamping member as follows. Sleeve 120 is slid over the upper or lower end of post 119 and to the desired location therealong. A threaded fastener 145 is then inserted into opening 136 via access opening 138, and into opening 139. As the fastener 145 is tightened, ring member 131 is moved towards the opposite ring member 130 to effectively clamp the post 119. The lowermost sleeve 120 is attached to the lower end of post 119 in the same manner as upper sleeve 120. The sleeves 120 are removed from post 119 in the reverse manner from that described above.

Referring to FIG. 1, post assembly 13 additionally includes an uppermost and generally tubular mounting sleeve 150 fixed to the upper end of post 119, and an uppermost post extension section 151. Post section 151 in the illustrated embodiment is of a diameter to allow same to telescope into the open upper end of post 119. Mounting sleeve 150 defines therein a threaded opening (not shown), into which a clamping knob 152 is received. Post section 151 is thus positioned at the desired height relative to post 119, and clamping knob 152 is then tightened so as to engage post section 151 and clamp same at the selected height relative to post 119. Post section 151 mounts thereon a support member 153, which in the illustrated embodiment defines a plurality of mounting openings therein for receiving terminal inner ends of hooks 154. Hooks 154 can be used for supporting thereon bags of IV fluid as illustrated in FIG. 1 in dotted lines, or other medical equipment. In this regard, it will be appreciated that the other types of medical equipment may be supported on post assembly 13 as mentioned above, such as patient monitors and the like which would be suitably mounted on post 119.

The transfer arrangement 10 according to the invention operates as follows. Pursuant to one method of operation, the post assembly 13 is installed on a patient transfer device by inserting collet 110 of lower receiver assembly 100 into the opening 16 defined in frame 15 of the patient transfer device 17. The bolt 116 is then tightened, which first causes wedge 114 (due to the steeper taper thereof) and then wedge 115 to move towards intermediate portion 111 of collet 110, which effectively causes the adjacent fingers 112 and 113 to expand outwardly against the walls of the opening 16 to lock the collet 110 and thus the lower receiver assembly 100 to the frame 15. The post assembly 13 is then lowered so as to insert lower sleeve 120 into lower receiver 101. The lowermost chamfered or tapered end 124 of the lower sleeve 120 helps to vertically align the lower sleeve 120 into the uppermost bore portion 95 of lower receiver 101. Continued lowering of sleeve 120 into lower receiver 101 eventually causes the tapered portion 127 of lower sleeve 120 to engage the angled support ridge 93 of lower receiver 101 (see FIG. 12) which effectively vertically supports lower sleeve 120 within lower receiver. The engagement of tapered portion 127 of sleeve 120 with ridge 93 as well as the engagement of intermediate section 125 of sleeve 120 with lowermost portion 90 of bore 89 firmly supports sleeve 120 and post 119 in a horizontal direction.

The patient is then transported to a care area (such as an intensive care unit (ICU)) via the patient transfer device 17, which now carries the post assembly 13. The post assembly 13, which may support thereon various types of medical equipment, such as IV-related devices, pumps, monitors, etc. is then transferred to the support 12 located in the ICU, for example. The positioning arm 11 mounted on support 12 is positioned laterally adjacent the post assembly 13. The transfer device 17, here a patient bed, is height adjustable manually or via an appropriately controlled motor or motors. Accordingly, the device 17, which carries post assembly 13 thereon, is raised until the upper sleeve 120 is essentially horizontally aligned with upper receiver 83, such that the tapered section 127 of upper sleeve 120 is positioned slightly above the uppermost surface 96 of upper receiver 83. The positioning arm 11 is then moved horizontally towards the upper sleeve 120 which allows section 125 of sleeve 120 to enter upper receiver 83 sidewardly through slit 85. Once sleeve 120 is fully inserted sidewardly into receiver 33, the device 17 is then lowered to allow full insertion of upper sleeve 120 into upper receiver 83, i.e. until tapered surface 127 of sleeve 120 is engaged with and supported on angled support ridge 93 of receiver 83, as shown in FIG. 12. The post assembly 13 is now supported via positioning arm 11 and support 12, and may be positioned in the care area at the desired location by manipulating positioning arm 11.

Once the post assembly 13 is positioned in the desired location in the care area as discussed above, if desirable or necessary, the clamping assemblies 49 may be utilized to hold the positioning arm 11 in the desired configuration. In this regard, the bolts 47 which extend through the respective pivot brackets 35 of arm 11 are suitably adjusted so as to pretension the pivot brackets 35 between top and bottom walls 26 and 27 of clevis 24 as desired. As such, the bolts 47 may be adjusted so that a set amount of friction exists at the pivot brackets 35 so that same will allow easy manipulation and repositioning of arm 11, but will maintain the respective arm segments 21 and 22 in position after same are manually positioned by the user. The clamping assemblies 49 may thus be used to provide an additional holding force at each of the pivot brackets 35, to firmly hold the arm 11 in position.

Since the respective clamping assemblies 49 operate in an identical manner, a description of operation of only one clamping assembly 49 is provided herein. The clamping assembly 49 is in the unlocked position when the clamp arm 63 is oriented generally vertically, as shown in dotted lines in FIG. 3. In this unlocked position, the pusher plate 55 is not exerting any significant force on the respective braking pins 75, and the pusher plate 55 is thus vertically movable relative to T-bolt 76. When the clamp arm 63 is rotated downwardly towards the respective arm segment 21 or 22 from the locked position, this causes the cams 67 defined on forks 66 to exert a downward force on the upper surface 60 of pusher plate 55, forcing pusher plate 55 and thus brake pins 75 downwardly into engagement with upper bearing plate 46. The force exerted by upper bearing plate 46 on pivot bracket 35 thus prevents rotation thereof. The clamping assembly 49 is moved from the locked position to the unlocked position in the reverse manner, i.e. by rotating clamp arm 63 upwardly which releases the brake pins 75 from the upper bearing plate 46.

When it is desirable to transport the patient from the care area, the post assembly 13 is transferred to the patient transfer device 17. The clamping assemblies 49, if in the locked position, are released as described above to allow manipulation of positioning arm 11. The arm 11 is then moved as necessary in a generally horizontal plane about the respective vertical axes defined at the respective pivot bolts 47 so as to vertically align the lower sleeve 120 with the lower receiver 101. The device 17 is then raised until the lower sleeve 120 of post assembly 13 is inserted into lower receiver 101. As mentioned above, the lower tapered end 124 of lower sleeve 120 helps to vertically align the sleeve 120 and receiver 101.

Raising of the device 17 is continued until the tapered surface 127 of sleeve 120 is engaged with and supported on the angled support ridge 93 of lower receiver 101. It will be appreciated that the device 17 must be raised to a height relative to the positioning arm 11 during transfer which will allow the upper sleeve 120 to be lifted at least a short vertical distance upwardly so as to place tapered surface 127 of upper sleeve 120 above the uppermost surface 96 of upper receiver 83. The device 17 may then be moved away from positioning arm 11, which will effectively cause upper post sleeve 120 to exit the upper receiver 83 sidewardly through the slot 85.

The transfer arrangement 10 according to the invention thus allows easy and rapid transfer of an equipment-supporting post assembly between two support structures, while requiring minimal personnel and effort from hospital staff. The positioning arm as described above is easily manipulated and is easily movable in a generally horizontal plane due to the configuration of the arm segments and the connections therebetween, which allows ready vertical alignment of the post sleeves and receivers.

Figure 17:
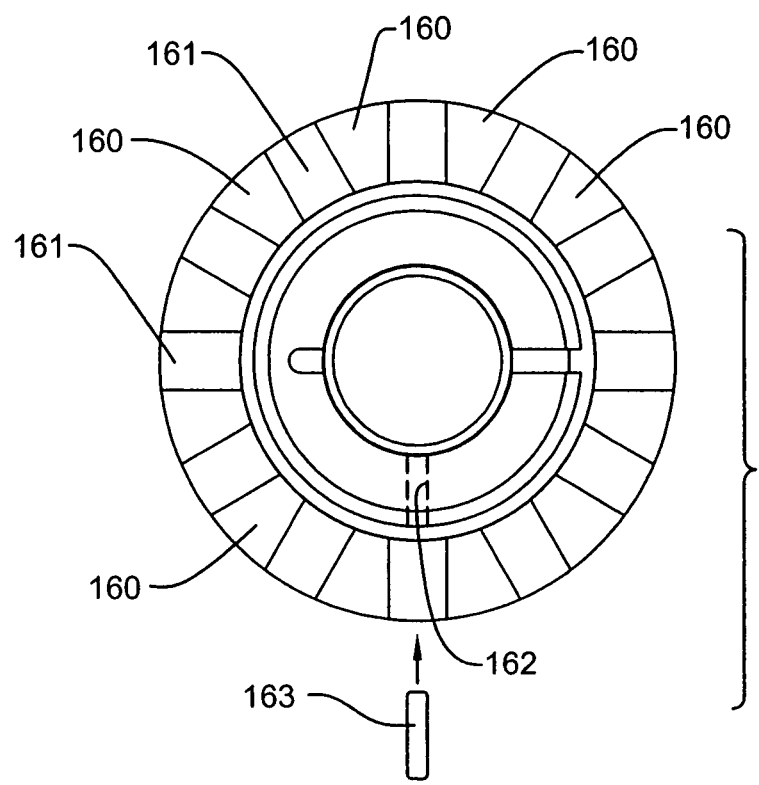
FIG. 17 is an enlarged plan view of the receiver of FIG. 16, and additionally including a post sleeve and post disposed therein.
Figure 16:
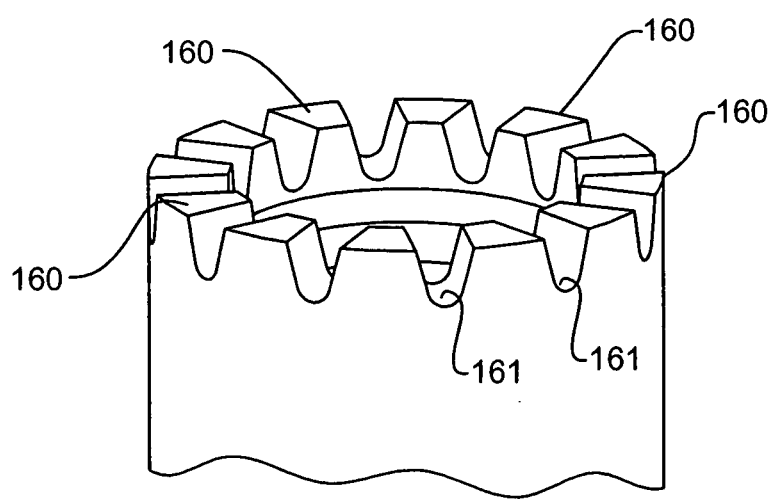
FIG. 16 is an enlarged fragmentary perspective view of the upper end of a receiver, according to an alternative embodiment.

FIGS. 16 and 17 illustrate an alternative embodiment of the receiver and post sleeves. Specifically, the upper and lower receivers 83 and 101 described above can alternatively be provided with a series of teeth or projections 160 which project upwardly from the uppermost ring-like edge thereof. The projections 160 are circumferentially spaced from one another such that a slot 161 is defined between each adjacent pair of projections 160. In this embodiment, the upper portions of the upper and lower post sleeves 120 described above are provided with an opening 162 which opens sidewardly through an outer surface of the sleeve, which slot 162 is configured to receive therein a pin 163. This embodiment operates in a similar manner as the above-described embodiment, but additionally provides a way to positively fix the rotational position of the post assembly relative to the respective upper and lower receivers. That is, when the post assembly is inserted into either the upper or lower receiver, the pin 163 mounted on the respective post sleeve will engage within a selected one of the slots 161 of the receiver and thus prevent rotation of the post assembly relative to the respective receiver.

Figure 18:
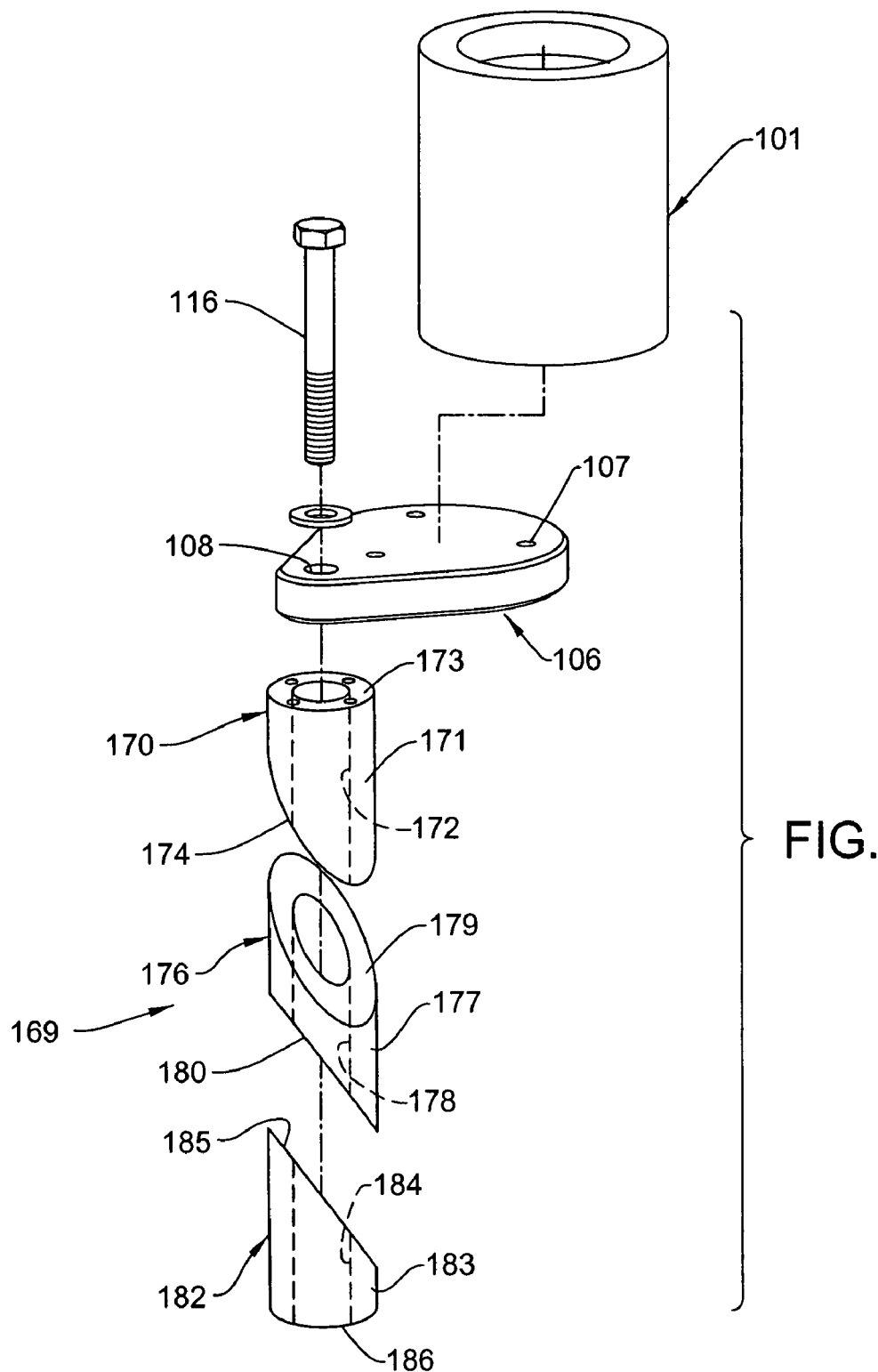
FIG. 18 is an enlarged exploded perspective view of a lower receiver assembly, according to an alternative embodiment.

FIG. 18 illustrates an alternative embodiment of the lower receiver assembly. This embodiment is identical to the lower receiver assembly illustrated in FIG. 13 and described above, except that the an alternative clamping arrangement 169 is provided for engaging within the opening 16 provided on the transfer device 17. Accordingly, the same reference numbers are utilized for identical or similar components.

The lower receiver assembly in this embodiment includes a plurality, and here three, of clamping wedges, all of which are generally tubular in shape. Upper clamping wedge 170 is defined by a cylindrical wall 171 which defines therein a threaded through bore 172. Cylindrical wall 171 defines an uppermost surface 173 which is essentially flat and horizontally oriented, and a lowermost surface 174 which is angled relative to the horizontal. Clamping arrangement 169 additionally includes an intermediate wedge 176 defined by a cylindrical wall 177. Wall 177 defines therein a through bore 178. Intermediate wedge 176 at opposite ends thereof includes uppermost and lowermost surfaces 179 and 180 which are angled relative to the horizontal. The angled surfaces 179 and 180 are skewed at approximately 120° from one another. A lowermost wedge 182 is also provided, and is likewise defined by a cylindrical wall 183 defining a through bore 184 therein, and includes an upper surface 185 angled relative to the horizontal, and a lower surface 186 which is flat and generally horizontally oriented.

In this embodiment, in order to fix the lower receiver assembly to the frame 15, the three wedges 170, 176 and 182 are stacked vertically in the order as shown, and the angled surfaces of the respective wedges are oriented in mating relation relative to one another so that they together define a cylindrical post. This post, as defined by the three stacked wedges, is then inserted into the frame opening 16, and the bolt 116 is inserted through mounting plate 106 and at least into the bore 172 of the uppermost wedge 170. As bolt 116 is tightened, the three wedges are pushed apart at approximately 120° intervals, and effectively wedge into the wall defining the opening 16 of frame 15 to fix lower receiver assembly to the frame 15. The above arrangement can thus accommodate a wide range of hole sizes.

Figure 19:
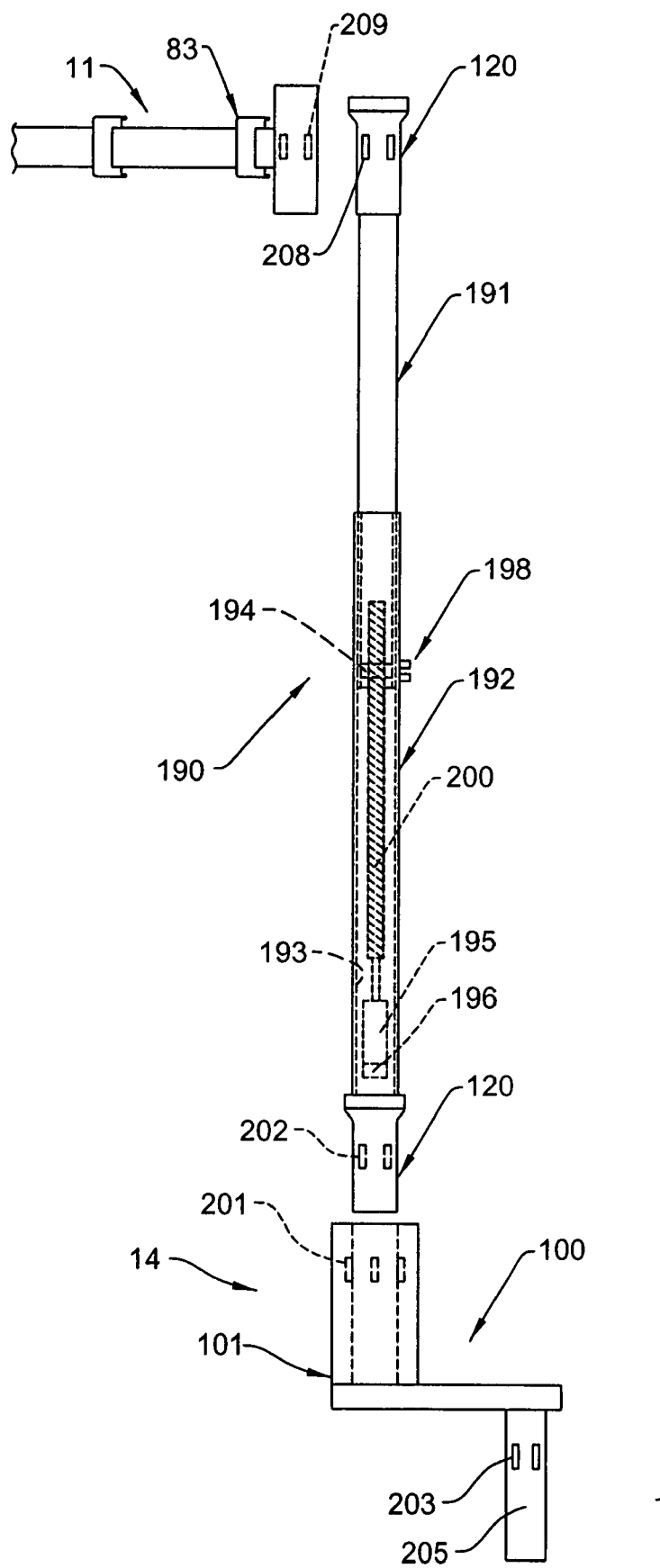
FIG. 19 is an exploded perspective view of an alternative embodiment of an equipment transfer arrangement.

FIG. 19 illustrates an alternative embodiment of a post assembly in accordance with the invention. The arrangement illustrated in FIG. 19 is essentially identical to the arrangement 10, except that the post assembly has been modified. The same reference numbers will accordingly be utilized in order to reference the same or similar components. Post assembly 190 in this embodiment includes an upper post section 191 and a lower post section 192 disposed in a telescoping manner with one another. The lower post section 192 is tubular in construction and defines an interior bore 193 in which a motor 195 is mounted adjacent a lower end thereof, which motor 195 may be electric or pneumatic. A battery 196 for providing power to motor 195 is also provided in lower post section 192. Motor 195 and battery 196 are shown schematically only in FIG. 19. Lower post section 192 also mounts thereon one or more control switches 198 for actuating motor 195. Lower post section 192 additionally mounts therein a threaded post or lead screw 200 which threadingly engages with a nut 194 fixed inside lower post section 192. The lower end of lead screw 200 is operatively connected to motor 195, such that actuation of motor 195 causes rotation of lead screw 200 relative to and within nut 194, which effectively pushes nut 194 and results in telescoping movement of upper post section 191 relative to lower post section 192 so as to lengthen or shorten the overall length of post assembly 190.

This embodiment accordingly does not rely on a height-adjustable transfer device 17 for raising or lowering the post assembly 190 to the proper vertical height, as in the prior embodiment. Accordingly, the overall length of the post assembly 190 is changed by actuating the motor 195 to drive lead screw 200 in the appropriate direction via control switches 198. For example, with post assembly 190 supported solely on positioning arm 11 and support 12 via upper sleeve 120, the post assembly 190 is vertically aligned with lower receiver 101 as described above, and the motor 195 is actuated in order to telescope upper post section 191 out of lower post section 192 and effectively lengthen the post assembly 190 by lowering the lower post section 192. Once the post assembly 190 is seated in lower receiver 101, continued lowering of the lower post section 192 will cause the upper post section 191 to unseat from upper receiver 83, and allow the upper sleeve 120 to exit the upper receiver 83 through the slot 85. Once installed on the frame 15, the post assembly 190 can then be adjusted to the desired overall height by actuating the motor 195 as necessary. The post assembly 190 is transferred from device 17 by actuating motor 195 so as to telescope upper post section 191 out of lower post section 192 to raise the upper post section 191 and allow upper sleeve 120 to engage in upper receiver 83 as described above.

The above embodiment can thus be utilized with non-height adjustable supports or transfer devices, since same does not rely on such device to position the post assembly at the proper vertical height for transfer. Further, the above arrangement may also be provided with electrical contacts 201 within lower receiver 101, as shown in dotted lines in FIG. 19, and mating electrical contacts 202 on lower sleeve 120 of post assembly 190. The contacts 201 provided within the lower receiver 101 would then be suitably wired to additional electrical contacts 203 provided on a clamping component 205 of lower receiver assembly 100 which mounts within the frame 15. The respective contacts 201 and 202 would thus electrically connect to one another when the post assembly 190 is mounted on frame 15 to charge the battery 196 through appropriate circuitry provided on the device 17. In addition, electrical contacts 208 may also be provided on upper post sleeve 120 which electrically connect to corresponding contacts 209 located within upper receiver 83 provided on arm 11. Thus, when post assembly 190 is mounted on arm 11 and support 12, battery 196 is charged through appropriate circuitry and wiring provided in arm 11 and support 12.

Figure 20:
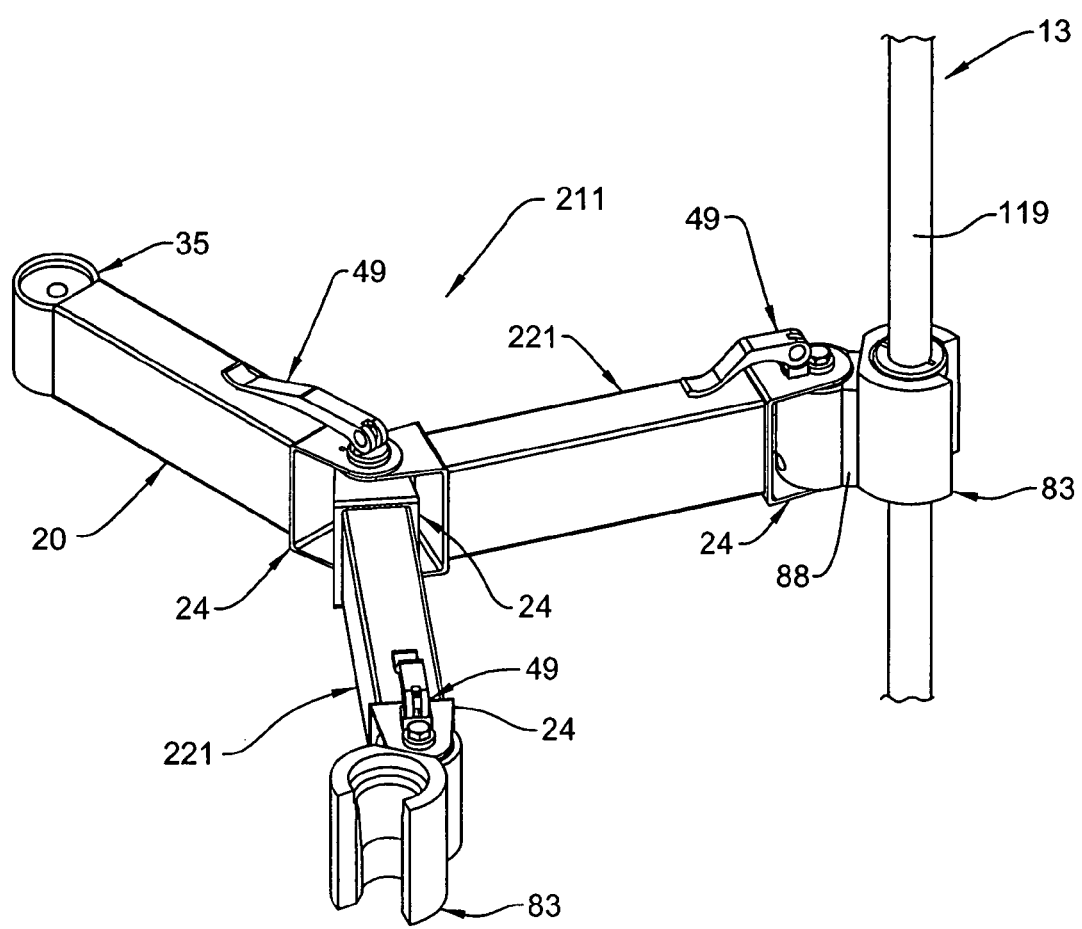
FIG. 20 is a perspective and fragmentary view of an alternative embodiment of the positioning arm.

FIG. 20 illustrates an alternative embodiment of the positioning arm. The positioning arm illustrated in FIG. 20 is similar to the positioning arm 11 described above, and thus the same or similar components are identified with the same reference numbers.

The positioning arm arrangement 211 shown in FIG. 20 differs from arm 11 described above in that the inner arm segment or link 20 thereof mounts a pair of outer arm segments or links 221 at its outer end, instead of a single outer arm segment (see outer arm segment 21 in FIG. 1). The outer arm segments 221 are identical to one another, and each mount thereon an upper receiver 83 at their outermost ends. Inner arm segment 20 is provided with a clevis 24, pivot bracket 35 and clamping assembly 49 as in the prior embodiment. However, the inner ends of the respective outer arm segments 221 each mount thereon a clevis 24. One clevis 24 of one outer arm segment 221 is mounted over the clevis 24 of the other outer arm segment 221 and inside the clevis 24 of the inner arm segment 20, and a pivot bracket 35 is then mounted between the top and bottom walls of the innermost clevis 24. The clamping arrangement 49 provided on the outer end of inner arm segment 20 is manipulatable as described above so as to lock or unlock the three arm segments relative to one another.

The embodiment shown in FIG. 20 is thus capable of supporting two post assemblies 13, one in each receiver 83 of the respective outer arm segments 221 (only one such post assembly 13 being shown in FIG. 20 for simplicity purposes). It will be appreciated that more than two outer arm segments, each with its own receiver, may be mounted to a single inner arm segment.

FIGS. 21-30 illustrate a freestanding cart and post assembly 300 according to the present invention, generally including a cart 301 which is configured to support a post assembly 302. Post assembly 302 is generally similar to post assembly 13, except at the upper end same includes additional structures for supporting additional equipment as discussed in detail below. In one embodiment, the cart 301 may be utilized to transfer a post assembly carrying medical equipment thereon between the patient transfer device 17 and the cart 301, so as to allow the patient to ambulate with their associated medical equipment.

Figure 21:
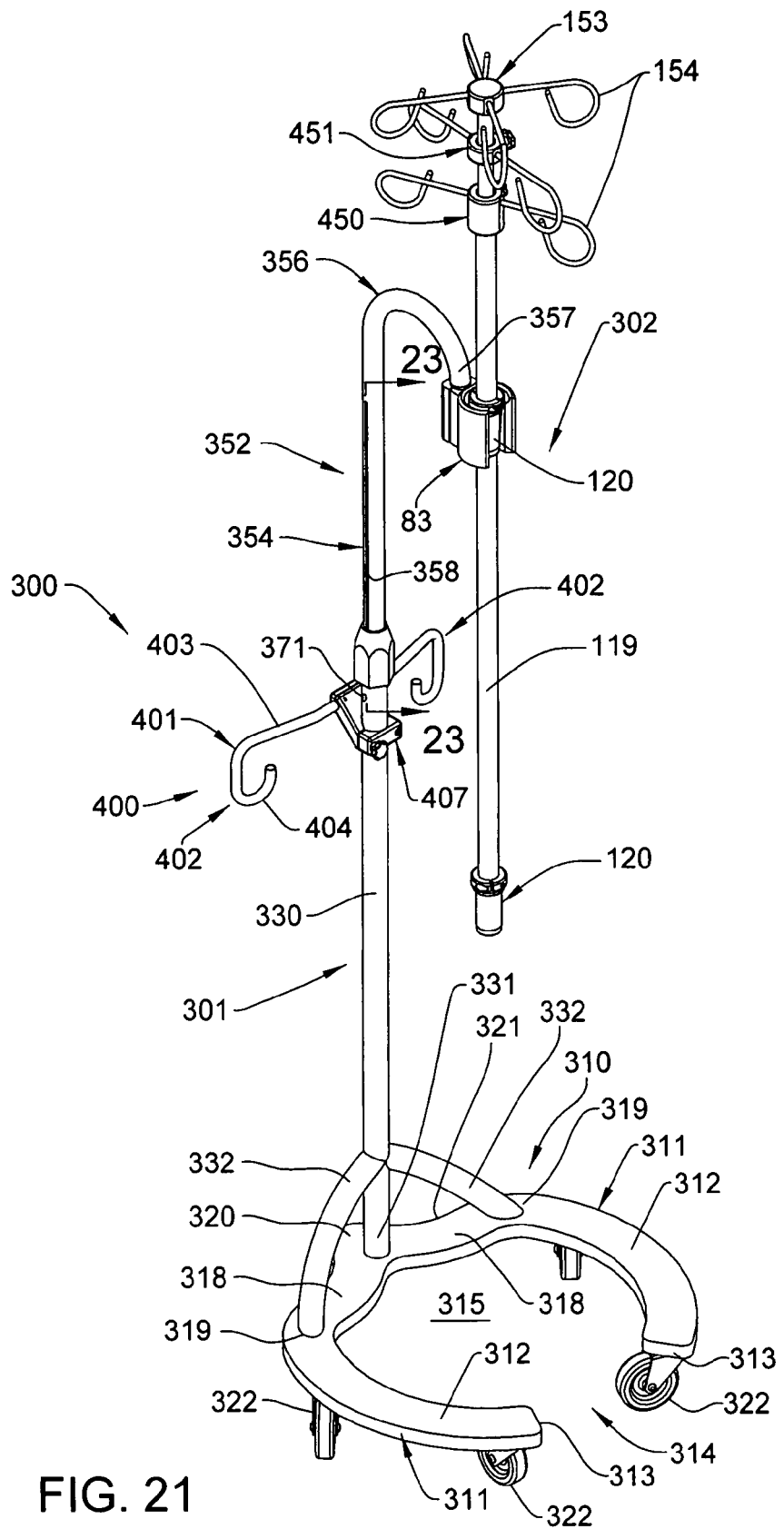
FIG. 21 is a perspective view of a freestanding cart arrangement which supports a post assembly according to the invention.

Referring to FIG. 21, cart 301 includes a base 310 defined by a pair of generally horizontally oriented legs 311. Legs 311 are in turn defined by respective front segments 312 which are generally arcuate in shape, curve inwardly towards one another and terminate at free ends 313. Ends 313 are laterally spaced from one another such that an opening 314 is disposed there between, which opening 314 defines a mouth of an inner generally circular space 315 defined between front leg segments 312. Legs 311 further include respective rear segments 318 which extend horizontally sidewardly away from their respective junctions 319 with front segments 312 and join to one another rearwardly at a nose 320. As shown in FIG. 21, rear leg segments 318 are inwardly arcuate so as to define respective recesses 321 which open rearwardly on opposite sides of nose 320. Configuring the base 310 in this manner is intended to discourage or prevent a user from standing or stepping on base 310. Legs 311 of base 310 mount thereon a plurality of rollers or casters 322 which are cantilevered downwardly therefrom for engagement with a support surface, such as a floor.

An elongate and upright main support post 330 which is generally tubular in configuration is fixed to and projects upwardly from base 310, generally in the area of nose 320. Main support post 330 has a lower end 331 fixed to base 310, and a pair of braces or supports 332 extend generally diagonally between main support post 330 and rear leg segments 318.

Figure 22:
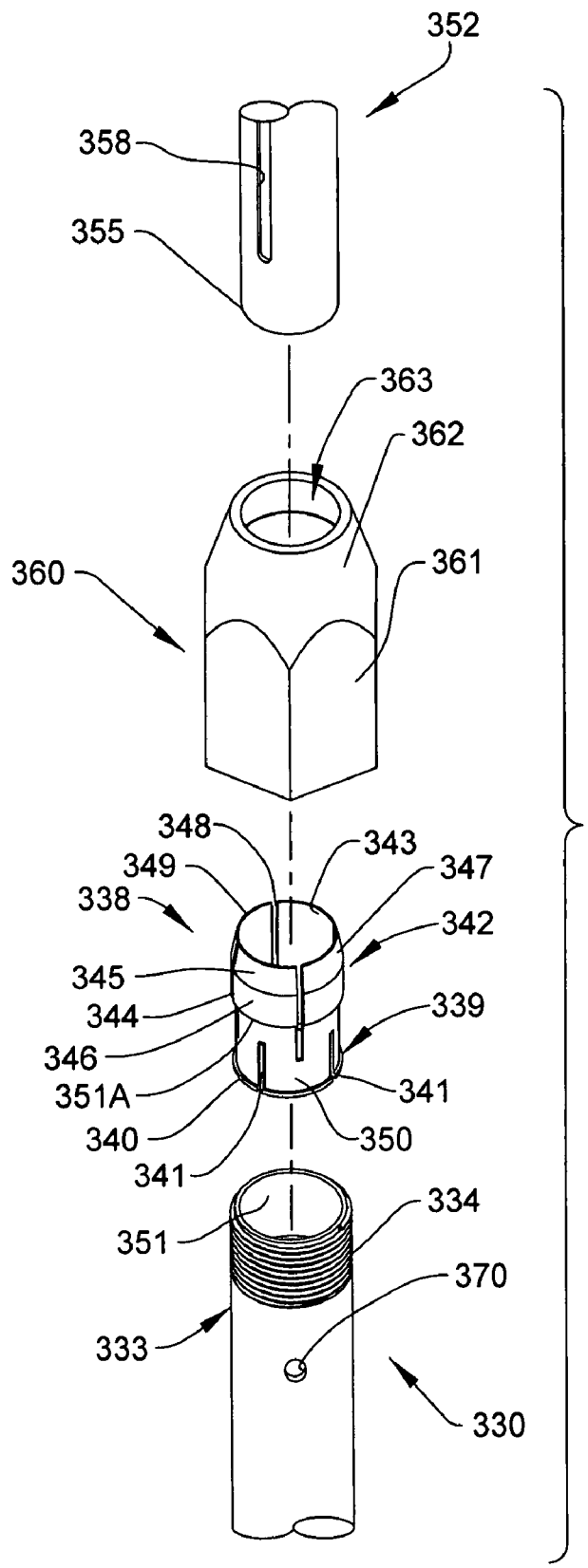
FIG. 22 is an enlarged, exploded and fragmentary perspective view of the connection between the main support post and the upper extension post of the cart.
Figure 23:
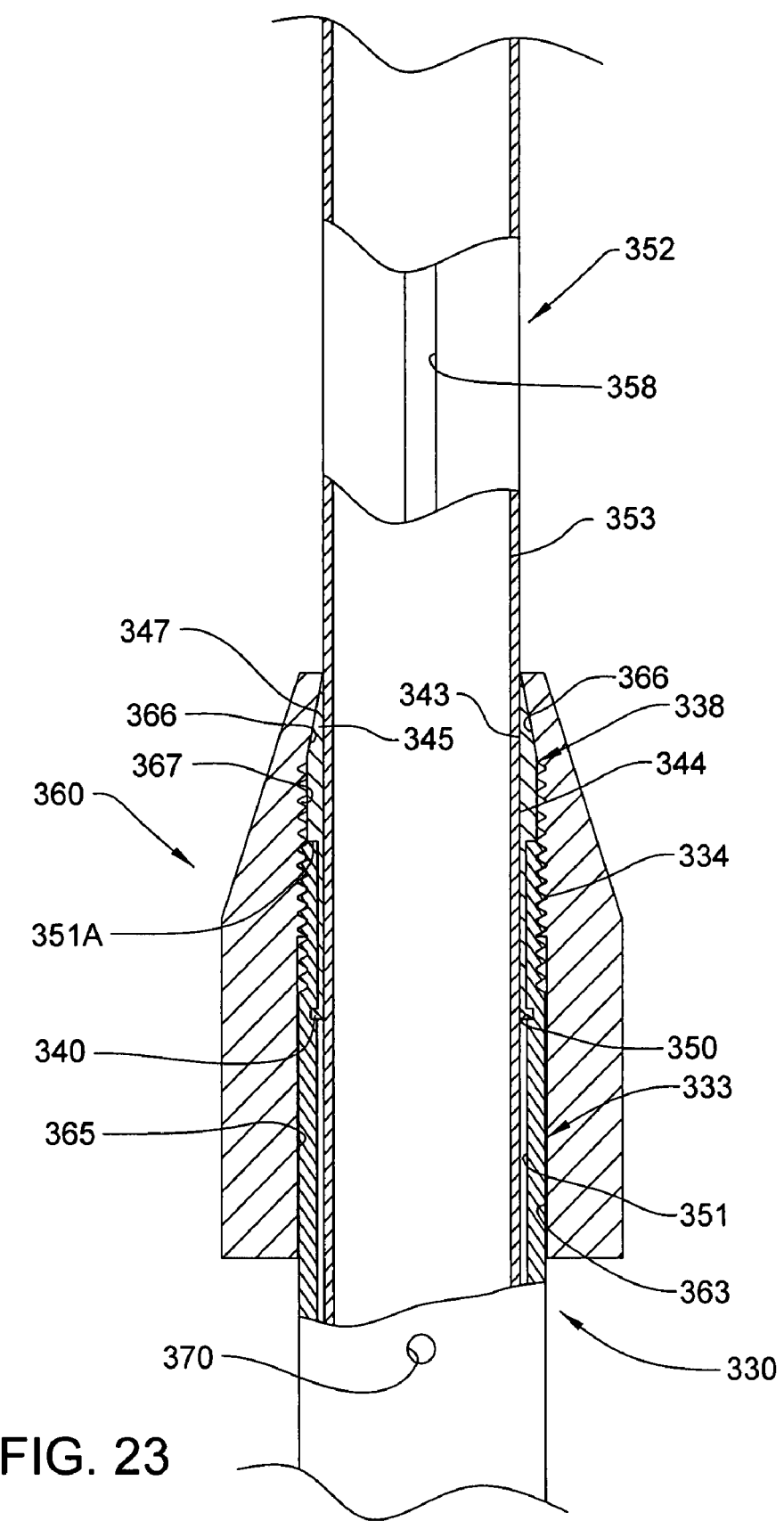
FIG. 23 is an enlarged vertical cross-sectional view taken generally along line 23-23 in FIG. 21.

Referring to FIGS. 22 and 23, main support post 330 has an upper end 333 which is provided with exterior threads 334. Upper end 333 is open, and is configured to receive therein a clamping sleeve 338. Clamping sleeve 338 includes a lower portion 339 which at its lower terminal end defines an annular flange 340. Flange 340 projects sidewardly outwardly from clamping sleeve 338. A plurality of slots 341 are formed in lower portion 339 in circumferentially spaced relation with one another. Clamping sleeve 338 additionally includes an upper portion 342, and an inner generally cylindrical surface 343 which extends throughout the length of sleeve 338. Upper portion 342 includes a lower section 344 and an upper section 345. Lower section 344 defines a cylindrical outer surface 346 which is joined to a frusto-conical outer surface 347 of upper section 345. A plurality of slots 348 extend through upper and lower sections 345 and 344, through part of lower portion 339, and open upwardly through a terminal edge of upper section 345. Slots 348 are circumferentially offset from slots 341. The respective portions of sleeve 338 disposed between two adjacent slots 348 define flexible fingers 349. Likewise, the respective portions of sleeve 338 defined between two adjacent slots 341 define flexible fingers 350.

As best shown in FIG. 23, main support post 330 defines therein an annular groove 350 along and within an inner wall surface 351 thereof, which is sized to receive flange 340 of clamping sleeve 338. In this regard, sleeve 338 is inserted downwardly into open upper end 333 of main support post 330 by exerting inward pressure on fingers 350 of lower portion 339 of sleeve 338, and continuing to push sleeve 338 downwardly until flange 340 seats within groove 350 which effectively causes fingers 350 to flex back outwardly so as to retain sleeve 338 at a fixed vertical height within post 330. When sleeve 338 is seated within the upper end 333 of post 330 as described above, upper portion 342 of sleeve 338 projects upwardly beyond the upper terminal edge of upper end 333 of post 330, and a step or shoulder 351A defined at a junction between upper and lower portions 342 and 339 of sleeve 338 is seated atop or abuts the terminal edge of main support post upper end 333.

Cart 301 further includes an upper and generally tubular extension post 352 defined by a tubular wall 353. Extension post 352 includes a lower and generally linear section 354 having a lower end 355 associated with and attached to main support post 330, and an upper curved section 356 joined to lower section 354 which upper curved section 356 has a terminal end 357 associated with post assembly 302. Due to the curvature of upper section 356, terminal end 357 thereof is spaced horizontally forwardly from linear section 354, which effectively positions post assembly 302 generally centrally above base 310 and stabilizes cart 301. Linear section 354 defines therein an elongate and longitudinally extending slot 358, which extends along the majority of the longitudinal extent of section 354.

The lower end 355 of extension post 352 is telescopingly engaged within the open upper end 333 of main support post 330, and specifically within the sleeve 338. A collet 360 is provided for the purpose of locking extension post 352 to main post 333. In this regard, collet 360 is generally sleeve-shaped and includes a lower part 361 joined to an upper generally frusto-conical shaped part 362, and a bore 363 extends throughout the length of the collet 360 through both upper and lower parts 362 and 361. Bore 363 has a lower bore part defined by an inner cylindrical surface 365, an upper bore part defined by an inner frusto-conical surface 366, and an intermediate bore part defined by a generally cylindrical threaded surface 367.

Main post 330 defines therein an opening 370 in upper end 333 thereof, downwardly from threads 334, which receives a pin 371 for a purpose as discussed below.

To assemble extension post 352 to main post 330, collet 360 is inserted over the lower end 355 of post 352, and lower end 355 is inserted into sleeve 338 at the upper end of main post 330. The rotational orientation of extension post 352 relative to main support post 330 is fixed by rotating extension post 352 within main post 330 and aligning slot 358 with opening 370 of main post 330. Pin 371 is then inserted through opening 370 and into slot 358. It will be appreciated that pin 371 may be a separate component from main post 330 or alternatively may be attached to main post 330 and spring-loaded such that pin 371 automatically engages within slot 358 of extension post 352 when post 352 is properly rotationally aligned with main post 330. Collet 360 is then telescoped over sleeve 338 and rotated so as to engage the interior threads 367 of collet 360 with the exterior threads 334 of main support post 330. Continued rotation of collet 360 causes inner frusto-conical surface 366 of collet 360 to engage with frusto-conical outer surface 347 of sleeve 338, which effectively causes fingers 349 of sleeve 338 to flex radially inwardly into abutting engagement with the outer surface of wall 353 of extension post 352 to fix same relative to main support post 330. The vertical height of extension post 352 relative to main post 330 can accordingly be adjusted by loosening collet 360, moving post 352 to the desired height and then re-tightening collet 360. The pin 371 and slot 358 maintains the extension post 352 aligned in the direction shown in FIG. 21.

Figure 24:
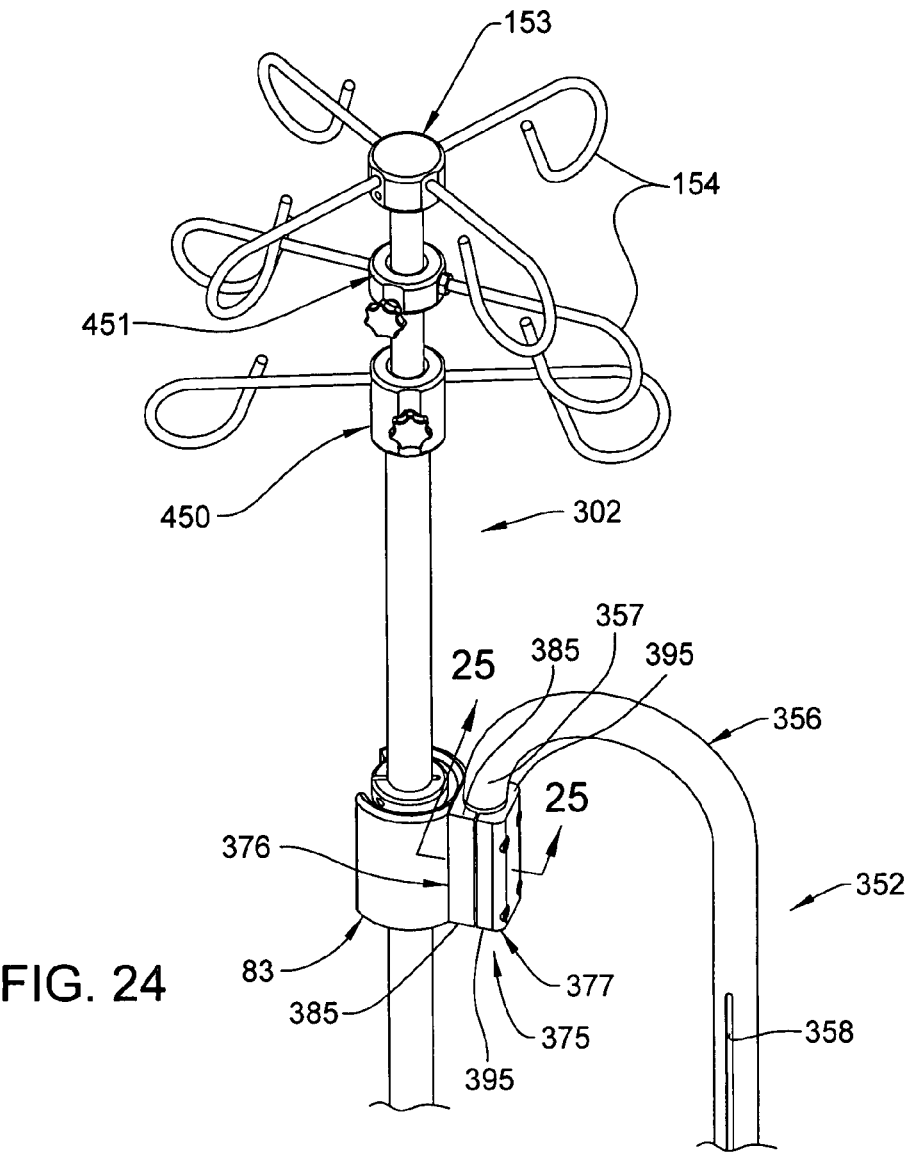
FIG. 24 is an enlarged and fragmentary rear perspective view of the upper end of the post assembly and the upper extension arm of the cart of FIG. 21.
Figure 25:
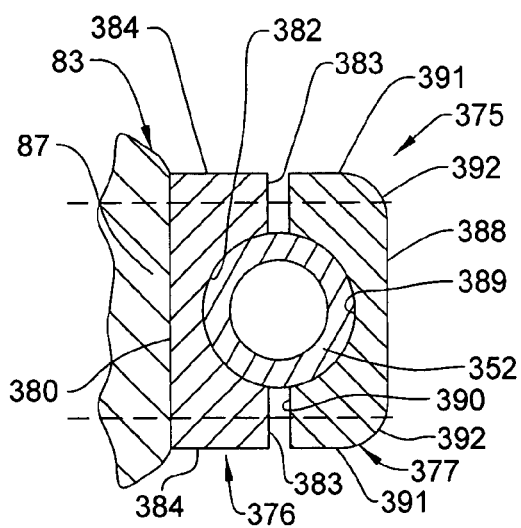
FIG. 25 is an enlarged cross-sectional view of the clamping arrangement of the upper extension arm of the cart taken generally along line 25-25 of FIG. 24.
Figure 26:
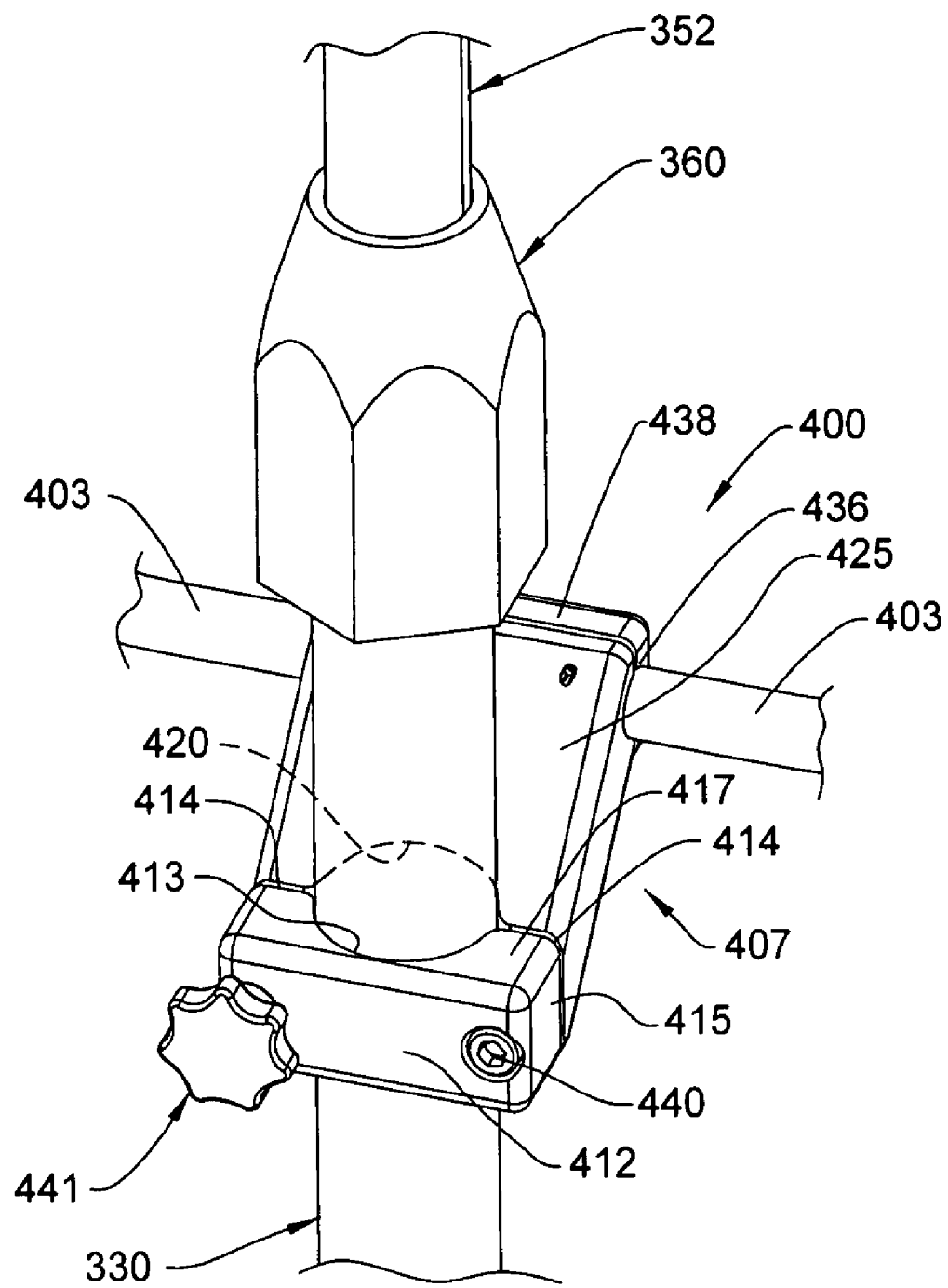
FIG. 26 is an enlarged and fragmentary front perspective view of the handle arrangement of the cart.

Referring now to FIGS. 24 and 25, upper terminal end 357 of extension post 352 mounts thereon a receiver substantially identical to receiver 83 discussed above and shown in isolation in FIG. 11. Accordingly, for purposes of simplicity, the same reference numbers are utilized to depict identical or similar components. Receiver 83 is fixed to terminal end 357 of extension post 352 by means of a clamping arrangement 375. Clamping arrangement 375 in the illustrated embodiment includes mating front and rear brackets 376 and 377. Front bracket 376 is defined by a flat outer surface 380 disposed in opposed relation with wall 87 of receiver 83, an inner surface defined by a semi-circular recess 382 and a pair of flat surfaces 383 disposed on opposite sides of recess 382. Front bracket 376 additionally includes a pair of generally parallel and spaced-apart side surfaces 384, and a pair of oppositely-facing (i.e. upwardly and downwardly) and generally parallel end surfaces 385.

Rear bracket 377 is defined by a flat outer surface 388 generally parallel to outer surface 380 of front bracket 376, an inner surface defined by a semi-circular recess 389, and a pair of flat surfaces 390 disposed on opposite sides of recess 389 in opposed relation with surfaces 383 of bracket 376. Rear bracket 377 also includes a pair of generally parallel and spaced apart side surfaces 391 which are joined to outer surface 388 by respective rounded edges 392, and oppositely-facing (i.e. upwardly and downwardly) generally parallel end surfaces 395.

Extension post 352 is assembled to receiver 83 by placing semi-circular recesses 382 and 389 of front and rear brackets 376 and 377 in facing relation with one another and over terminal end 357 of extension post 352, and by placing wall 87 of receiver 83 in abutting relation with outer surface 380 of front bracket 376. Brackets 376, 377 and receiver 83 (with end 357 of post 352 sandwiched between brackets 376 and 377) are then secured to one another with fasteners which extend through correspondingly-located openings defined in brackets 376, 377 and receiver 83. These fasteners and openings are shown diagrammatically only in dotted lines in FIG. 25. Tightening of the fasteners effectively clamps extension post 352 between brackets 376 and 377 and fixes receiver 83 thereto.

Figure 27:
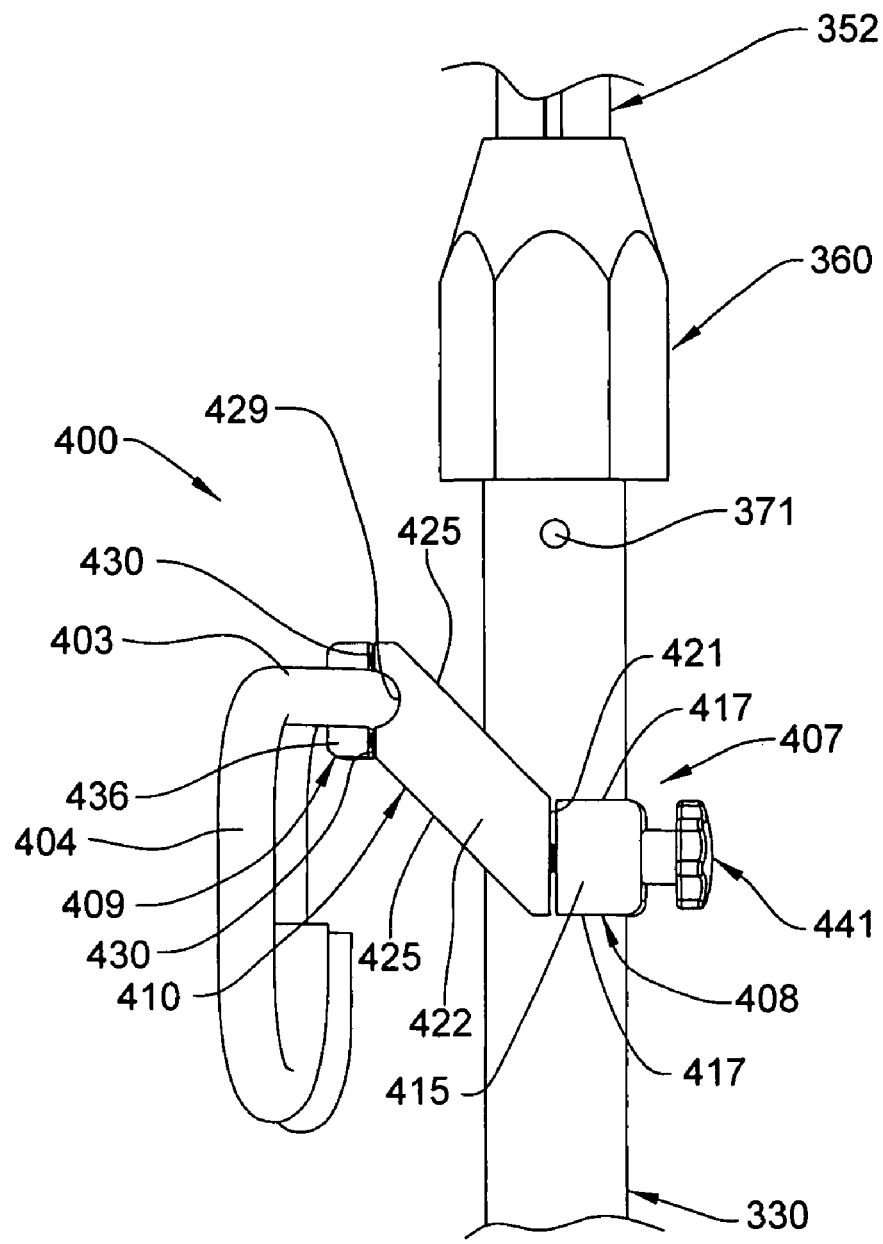
FIG. 27 is an enlarged and fragmentary side view of the handle arrangement of the cart.
Figure 28:
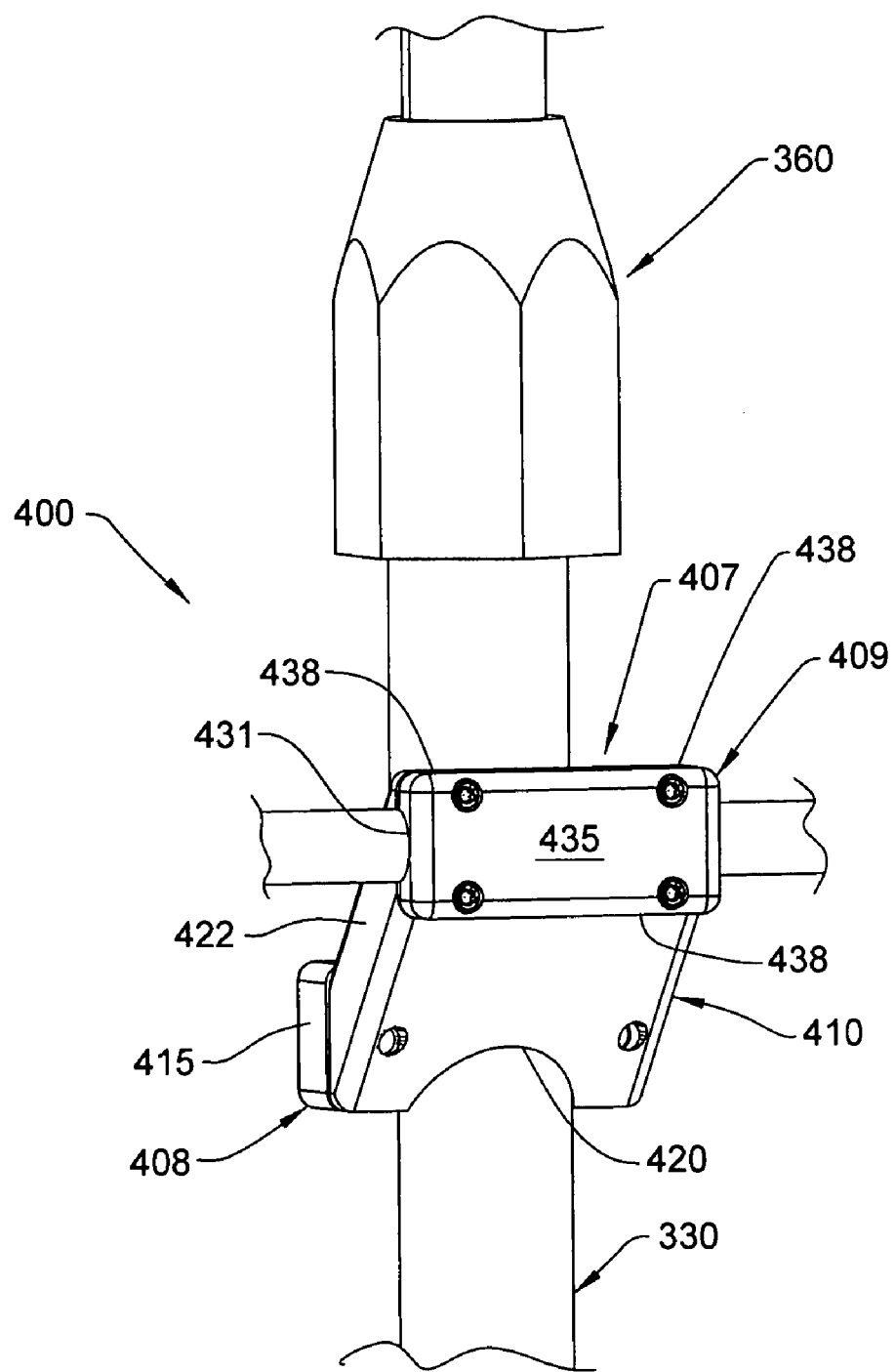
FIG. 28 is an enlarged and fragmentary rear perspective view of the handle arrangement of the cart.
Figure 29:
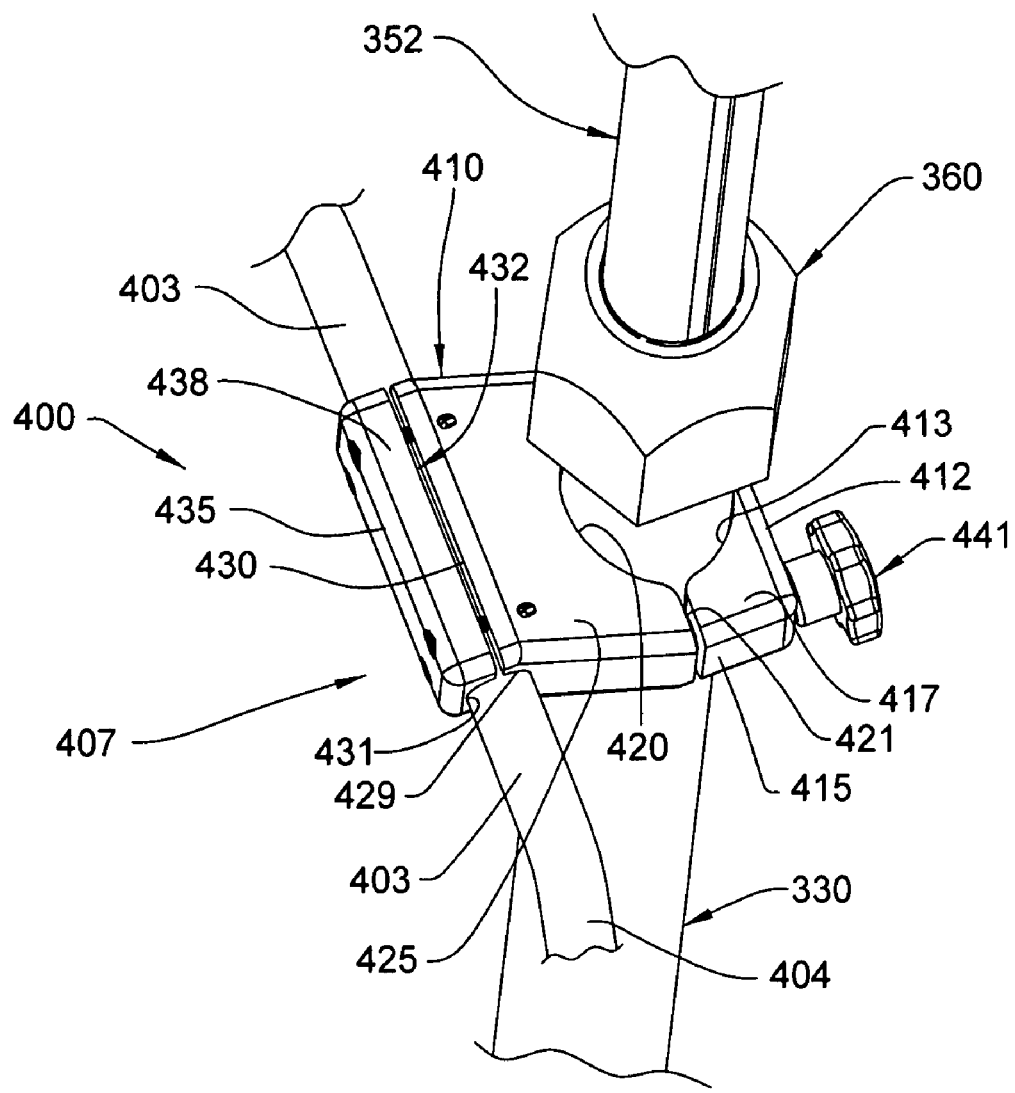
FIG. 29 is an enlarged and fragmentary top perspective view of the handle arrangement of the cart.

With reference to FIGS. 21 and 26-29, cart 301 includes a handle arrangement 400 provided on main support post 330 for the purpose of manipulating the cart 300. Handle arrangement 400 includes an elongate handle bar 401 having a pair of handles 402 which project sidewardly on respective opposite sides of the main support post 330. Each handle 402 includes a generally linear section 403 having an outer end from which a further hook-shaped handle section 404 projects either downwardly as shown, or alternatively handle section 404 may project upwardly. Each section 404 curves downwardly and then back upwardly, as best shown in FIGS. 21 and 27, so as to define a space for receiving a user's hand. This shape allows the user to rest the hand within the "hook", while holding the vertical part of the hook within the fingers. It will be appreciated that the handle bar 401 may be provided with a protective cover for user comfort, which cover is not shown here.

Handle arrangement 400 is mounted on main support post 330 by means of a mounting bracket 407. In the illustrated embodiment, mounting bracket 407 is of a three-part construction, and includes a lower front section 408, an upper rear section 409 and an intermediate section 410 which extends in an angled orientation between and interconnects front and rear sections 408 and 409. Lower front section 408 has a generally flat front face 412 and an oppositely oriented rear face defining a semi-circular recess 413 and a pair of flat surfaces 414 generally parallel to front face 412 and disposed on opposite sides of recess 413. Lower section 408 additionally includes a pair of generally parallel and upright side surfaces 415, and oppositely-facing (i.e. upwardly and downwardly) generally flat end surfaces 417. Side surfaces 415 are joined to end surfaces 417 and front face 412 by generally rounded edges, and end surfaces 417 are joined to front face 412 by rounded edges.

Intermediate section 410 of mounting bracket 407 is defined by a flat front face defined by a semi-circular recess 420 and a pair of generally flat surfaces 421 disposed on opposite sides of recess 420. A pair of generally parallel and upright side surfaces 422 are defined on intermediate section 410, as well as a pair of oppositely-facing and generally flat top and bottom end surfaces 425. It will be appreciated that end surfaces 425 are angled relative to the horizontal, such that intermediate section 410 angles downwardly as same projects frontwardly away from rear section 409 of mounting bracket 407. Side surfaces 422 join to end surfaces 425 via rounded edges in the illustrated embodiment. Intermediate section 410 additionally includes a rear face defined by a semi-circular recess 429, and a pair of upper and lower horizontally elongate surfaces 430 respectively disposed above and below recess 429.

Upper rear section 409 of mounting bracket 407 includes a front face defined by a semi-circular recess 431 and a pair of surfaces 432 respectively disposed above and below recess 431, and a generally flat rear face 435 which is generally parallel to surface 412 of lower section 408. Rear section 409 further includes a pair of parallel side surfaces 436, and upper and lower generally flat surfaces 438. Side surfaces 436 are joined to upper and lower surfaces 438 as well as to surface 435 of rear face via rounded edges in the illustrated embodiment.

To assemble handle arrangement 400, upper rear section 409 and intermediate section 410 are placed so that their respective semi-circular recesses 431 and 429 are in facing relationship with straight section 403 of handle bar 401 sandwiched therebetween. Fasteners are then utilized to interconnect upper rear section 409 and intermediate section 410, so that section 403 of handle bar 401 is clamped between the opposed sections 409 and 410. Handle arrangement 400, in one embodiment, is assembled to main support post 330 prior to fixing extension post 352 to main support post 330. In this regard, lower front section 408 and intermediate section 410 are placed so that their respective semi-circular recesses 413 and 420 face one another so as to define an opening for receiving main support post 330. These sections 408 and 410 are then fastened to one another. Specifically, a fastener 440 extends between lower section 408 and intermediate section 410, and a clamping knob 441 having an associated screw extending between sections 408 and 410 is mounted on lower section 408. The handle arrangement 400 is then telescoped or inserted over the upper end 333 of main support post 330, and clamping knob 441 is tightened so as to fix handle arrangement 400 on main support post 330. The user can adjust the vertical height of handle arrangement 400 by loosening clamping knob 441, moving handle arrangement 400 to the desired height on support post 330, and then tightening clamping knob 441.

Figure 30:
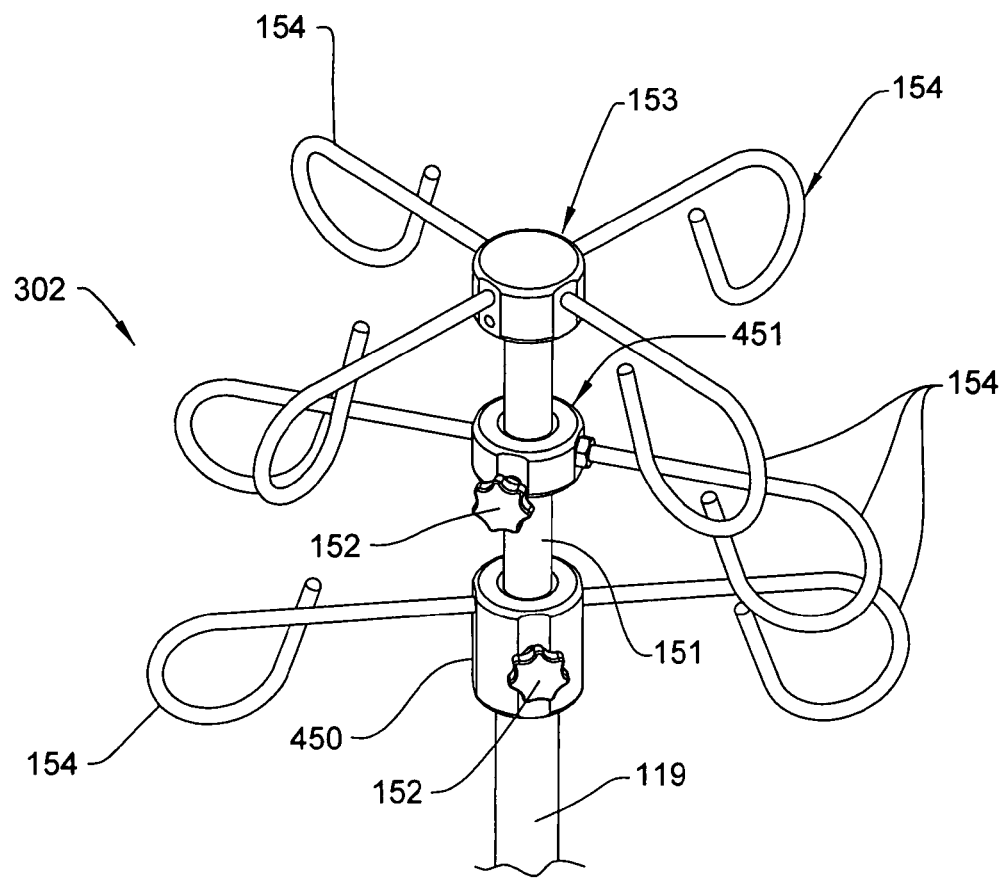
FIG. 30 is an enlarged and fragmentary view of the upper end of the post assembly of FIG. 21.

Turning now to post assembly 302, and with reference to FIGS. 21 and 30, same is generally similar to post assembly 13 discussed above, and the same reference numbers are accordingly utilized for the same or similar components. Post assembly 302 differs from post assembly 13 in that same includes a mounting sleeve 450 (similar to mounting sleeve 150) which not only allows vertical height adjustment of post extension section 151 relative to post 119, but also includes additional hooks 154 for supporting medical equipment. Further, post assembly 302 includes an additional intermediate mounting sleeve 451 mounted on post extension section 151 vertically between support member 153 and mounting sleeve 450. Intermediate mounting sleeve 451 defines therein a threaded opening into which a clamping knob 152 is disposed. The vertical height of intermediate mounting sleeve 451 and the rotational orientation of hooks 154 provided on sleeve 451 are therefore adjustable relative to support member 153 and the lower mounting sleeve 450 by manipulating clamping knob 152 of sleeve 451.

Figure 31:
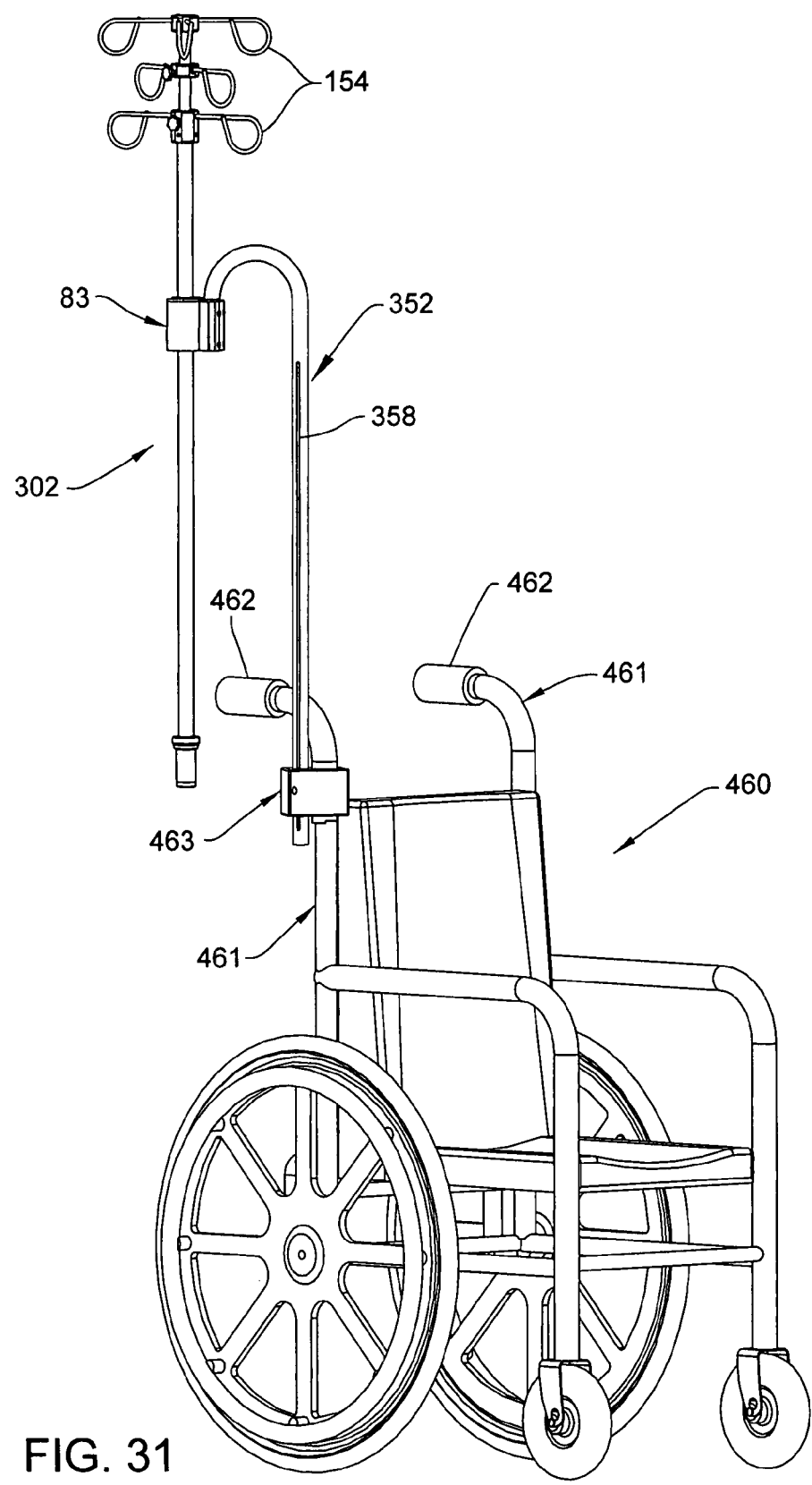
FIG. 31 is a perspective view of a wheelchair and post-mounting arrangement for the post assembly according to the invention.
Figure 32:
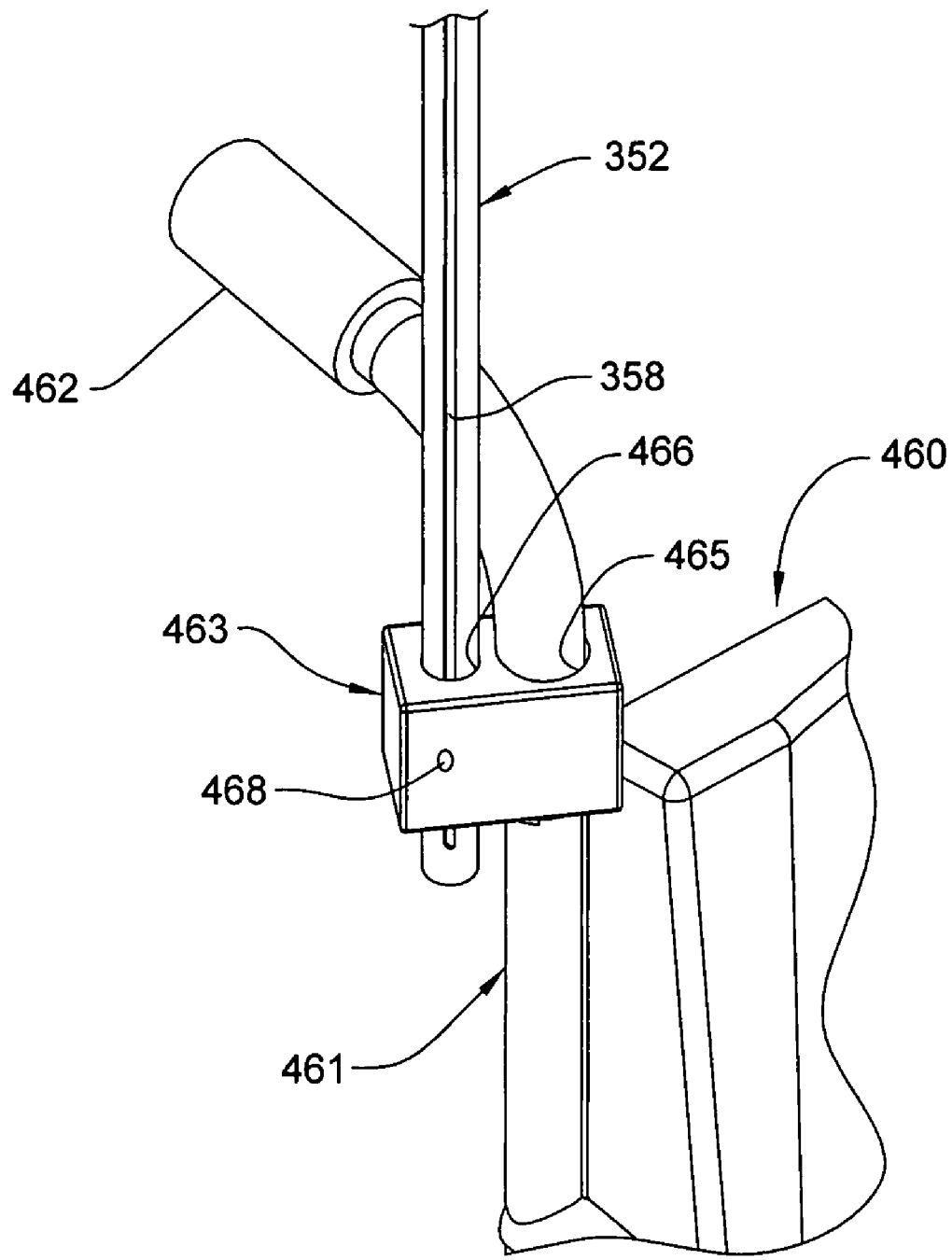
FIG. 32 is an enlarged and fragmentary view of the post-mounting arrangement of the wheelchair of FIG. 31.

FIGS. 31 and 32 illustrate a patient transfer device in the form of a wheelchair 460, which wheelchair 460 is equipped to support the post assembly 302 when transfer from a patient bed 17 to a wheelchair 460 is desirable or necessary.

Wheelchair 460 includes a pair of upright frame members 461 which at their upper terminal ends define respective handles 462 for manipulating the wheelchair 460. Wheelchair 460 mounts thereon a post, which is identical to upper extension post 352 of cart 301 discussed above. In this regard, extension post 352 is fixed to one of frame members 461 by a mounting bracket 463 supported on frame member 461. Bracket 463 defines a pair of openings therein, wherein one of these openings 465 receives frame member 461, and the other opening 466 receives the lower end of extension post 352 therein. It will be appreciated that bracket 463 may have many different forms. For example, bracket 463 may be embodied by a pair of opposed clamps which are fastened to one another so as to clamp both frame member 461 and extension post 352 therebetween. Alternatively, bracket 463 may be welded directly to frame member 461, and a clamping knob provided so as to clamp extension post 352 to bracket 463 and allow height adjustment of post 352. In addition, a pin 468 may be provided which extends through an opening in bracket 463, into opening 466 and into slot 358 of post 352 so as to rotationally lock the post 352 relative to pin 468.

In use, with post assembly 302 or 13 installed on patient transfer device or bed 17, when the patient desires to ambulate with his or her associated medical equipment, the cart 301 is moved into position close to device 17. It will be appreciated that mouth 314 and space 315 defined on base 310 of cart 301 allows the cart 301 to straddle the leg or caster typically provided on the bed 17. The bed 17 is then raised to a suitable height so as to raise the upper sleeve 120 of the post assembly 13, 302 slightly above the cart receiver 83, and then the cart 301 is moved laterally towards the bed 17 so as to cause the upper sleeve 120 of post assembly 13, 302 to be moved laterally into the cart receiver 83 through the slot 85 defined therein. The bed 17 is then lowered so as to lower and seat the upper sleeve 120 of the post assembly 13, 302 within the cart receiver 83 so that the post assembly 13, 302 is supported on cart 301. The patient is then able to exit the bed 17 and ambulate with their associated equipment now fully supported on cart 301.

When it is desirable for the patient to return to the patient bed 17, the cart 301 is positioned adjacent the bed 17 so that the lower sleeve 120 of post assembly 13, 302 is vertically aligned with lower receiver 101 of bed 17. The bed 17 is then raised until the lower sleeve 120 fully engages with the lower receiver 101 and the post assembly 13, 302 is raised by the bed 17 relative to receiver 83 of cart 301. The bed 17 is raised until the upper sleeve 120 of post assembly 13, 302 is slightly above the upper edge of cart receiver 83, and then the cart 301 is moved away from the bed 17 so as to allow the upper sleeve 120 to exit cart receiver 83 laterally through slot 85 so that post assembly 13, 302 is fully supported on bed 17.

Transfer of the post assembly 13, 302 from the patient bed 17 to the wheelchair 460 is carried out by positioning the wheelchair 460 close to the patient bed 17, and performing the same steps as indicated above relative to the cart 301.

It will be appreciated that while the illustrated embodiment depicts a cart 301 which is utilized to transfer post assembly 13, 302 between itself and a height-adjustable patient transfer device 17, cart 301 may alternatively be configured to receive post assembly from or transfer post assembly to, the transfer arrangement 10 illustrated in FIG. 1 or wheelchair 460. In this embodiment, the extension post 352 of cart 301 may be vertically adjustable relative to main support post 330, so as to allow the cart receiver 83 to be positioned vertically adjacent receiver 83 of arm 11 or wheelchair 460, so that the post assembly can be easily manually transferred between receivers 83. Alternatively, the position of service head 12 of arrangement 10 may be vertically adjustable so as to position arm receiver 83 adjacent cart receiver 83 or chair receiver 83 for transfer of the post assembly. Still further, the extension post 352 of transfer device or wheelchair 460 may be vertically adjustable relative to bracket 463 so as to allow vertical positioning of chair receiver 83 for transfer of post assembly to arrangement 10 or cart 301.

All of the above embodiments may be provided with proximity sensors for the purpose of detecting obstacles during transport of the patient. Such sensors may activate an alarm to alert the caregiver of obstacles, or may communicate with a braking arrangement provided on the transfer device so as to cause braking of same.

Although a particular preferred embodiment has been disclosed in detail for illustrative purposes, it will be recognized that variations or modifications of the disclosed apparatus, including the rearrangement of parts, lie within the scope of the present invention.

What is claimed is:

1. An arrangement for transferring medical equipment between first and second supports, said arrangement comprising:
    a positioning arm having a first end configured for connection to a first support and a second end spaced from said first end and mounting thereon a generally sleeve-shaped connector element, said positioning arm including first and second articulated arm segments disposed between said first and second ends; and a medical equipment support assembly including a generally upright post having upper and lower vertically-spaced ends and for mounting medical equipment thereon, said medical equipment support assembly further including a post connector element connected to said post, disposed between said upper and lower ends of said post, and removably engaged within said sleeve-shaped connector element, said sleeve-shaped connector element opening sidewardly to permit sideward insertion or removal of said post during transfer of said equipment support assembly between the first support and the second support.

2. The arrangement of claim 1, wherein the second support is a patient support, said arrangement further comprising an upwardly opening connector element assembly configured for support on a frame of a patient support.

3. The arrangement of claim 2, wherein said post connector element is a first connector element and a second connector element mounted on said lower end of said post is shaped for cooperation with, and supportive engagement on, said connector element assembly such that said medical equipment support assembly is transferable between said arm and a patient support and is supportable on said arm and a patient support.

4. The arrangement of claim 3, wherein said post is vertically-height adjustable to permit selective vertical positioning of one of said first and second connector elements relative to a selected one of said connector element assembly and said sleeve-shaped connector element.

5. The arrangement of claim 3, wherein said first and second connector elements each include a generally cylindrical portion and upper and lower portions disposed at respective upper and lower ends of said cylindrical portion, said upper portion defining thereon a support surface which projects horizontally beyond an outer surface of said cylindrical portion.

6. The arrangement of claim 5, wherein said post defines a central vertical axis, and said support surface of each said first and second connector element is angled such that same diverges inwardly towards the central vertical axis as same projects downwardly.

7. The arrangement of claim 6, wherein said sleeve-shaped connector element of said arm and said connector element assembly each include a sidewall defining a vertically oriented opening therein, said sidewall defining an interior angled support surface disposed for supportive engagement with said angled support surface of a corresponding said first or second connector element when said corresponding said first or second connector element is disposed in said opening.

8. The arrangement of claim 1, wherein said first and second arm segments are connected to one another for articulating movement about a generally vertically oriented axis to permit movement of said positioning arm in a generally horizontal plane and selective positioning of said sleeve-shaped connector element.

9. The arrangement of claim 8, wherein said sleeve-shaped connector element is pivotably mounted on said second end of said arm for pivoting movement about a generally vertically oriented axis.

10. The arrangement of claim 8, wherein said first and second arm segments include terminal ends which are connected to one another by a pivot bracket defining the vertically oriented axis, and said pivot bracket incorporates a locking mechanism which when engaged fixes said first and second arm segments in selected positions relative to one another.

11. The arrangement of claim 1, wherein said post connector element includes a generally cylindrical portion and upper and lower portions disposed at respective upper and lower ends of said cylindrical portion, said upper portion defining thereon a support surface which projects horizontally beyond an outermost surface of said cylindrical portion.

12. The arrangement of claim 11, wherein said post defines a central vertical axis, and said support surface is angled such that same diverges inwardly towards the central vertical axis as same projects downwardly.

13. The arrangement of claim 1, wherein said post connector element is a first connector element, and a second connector element is at said lower end of said post and is configured for cooperation with the second support when said support assembly is supported thereon.

14. The arrangement of claim 13, wherein said first and second connector elements are substantially identical in configuration.

15. The arrangement of claim 1, wherein said sleeve-shaped connector element is defined by a generally upright sidewall having a pair of adjacent free edge portions spaced horizontally from one another to define a horizontally-sidewardly opening slot therebetween, said slot extending vertically through the entire vertical extent of said sleeve-shaped connector element and being sized to receive said post therein or allow passage of said post therefrom during transfer of said medical equipment support assembly between the first and second supports.

16. The arrangement of claim 1, further including a cart having a base for supportive engagement with a floor and a support column having a lower end fixed to said base, said support column extending in a generally upright manner from said base and mounting thereon a generally sleeve-shaped cart connector element configured for cooperation with said post connector element to permit support of said medical equipment support assembly on said cart.

17. The arrangement of claim 16, wherein said support column of said cart includes an upper portion connected to said lower end and vertically adjustable relative thereto, said cart sleeve-shaped connector element being mounted on a free end of said upper portion of said support column.

18. The arrangement of claim 17, wherein said upper portion of said support column includes a generally straight portion disposed adjacent said lower end and a curved portion which projects sidewardly away from an upper end of said straight portion to said free end, said free end being positioned generally centrally over said base.

19. The arrangement of claim 18, wherein said base is defined by a pair of legs which are connected to said support column and project sidewardly away therefrom, said legs having respective free ends spaced from one another to define an opening therebetween to permit said cart to straddle a leg of a patient support during transfer of said medical equipment support assembly between said cart and a patient support.

20. A medical equipment transfer arrangement comprising:
 a horizontally elongate positioning arm having a first end fixed to a support member and a second end remote from said first end, said second end mounting thereon a receiver element, said positioning arm having first and second articulated arm segments disposed between said first and second ends;
 a receiver assembly for mounting to a patient support having a rigid frame and defining a support surface for a patient, said receiver assembly having an upwardly-opening receiver element; and a medical equipment support assembly including a generally vertically oriented post configured for supporting medical equipment thereon, said post having upper and lower vertically-spaced ends, said medical equipment support assembly further including a first connector element mounted on said post between said upper and lower ends and shaped for cooperation with, and supportive engagement on, said receiver element of said arm, said receiver element of said arm opening sidewardly to permit sideward insertion or removal of said post during transfer of said equipment support assembly between said arm and a patient support, and said medical equipment support assembly further including a second connector element mounted on said lower end of said post, said second connector element being shaped for cooperation with, and supportive engagement on, said receiver assembly such that said medical equipment support assembly is supportable on said arm and a patient support.

21. The arrangement of claim 20, further including a cart having a base disposed for supportive engagement with a floor and a column projecting in a generally upright manner from said base, said column mounting thereon a cart receiver element, said first connector element of said post being shaped for cooperation with, and supportive engagement with, said cart receiver element of said cart such that said medical equipment support assembly is transferable between said arm, said cart and a patient support and is supportable on said arm, said cart and a patient support.

* * * * *